United States Patent
Park et al.

(10) Patent No.: US 10,844,092 B2
(45) Date of Patent: Nov. 24, 2020

(54) PEPTIDE FOR PROMOTING REGENERATION OF DENTIN OR DENTAL PULP TISSUE

(71) Applicant: HysensBio Co., Ltd., Seoul (KR)

(72) Inventors: Joohwang Park, Incheon (KR); Jihyun Lee, Seoul (KR)

(73) Assignee: HysensBio Co., Ltd., Seoul (KR)

( * ) Notice: Subject to any disclaimer, the term of this patent is extended or adjusted under 35 U.S.C. 154(b) by 53 days.

(21) Appl. No.: 16/259,458

(22) Filed: Jan. 28, 2019

(65) Prior Publication Data

US 2019/0153033 A1 May 23, 2019

Related U.S. Application Data

(62) Division of application No. 15/838,957, filed on Dec. 12, 2017, now Pat. No. 10,428,110.

(30) Foreign Application Priority Data

Dec. 27, 2016 (KR) .................. 10-2016-0180408

(51) Int. Cl.

| | | |
|---|---|---|
| C07K 7/06 | (2006.01) |
| A61P 19/00 | (2006.01) |
| A61Q 11/00 | (2006.01) |
| A61K 8/64 | (2006.01) |
| A61K 47/62 | (2017.01) |
| A61K 38/00 | (2006.01) |

(52) U.S. Cl.
CPC .................. *C07K 7/06* (2013.01); *A61K 8/64* (2013.01); *A61K 47/62* (2017.08); *A61P 19/00* (2018.01); *A61Q 11/00* (2013.01); *A61K 38/00* (2013.01)

(58) Field of Classification Search
None
See application file for complete search history.

(56) References Cited

U.S. PATENT DOCUMENTS

| 8,222,216 B2 | 7/2012 | Hamada et al. |
| 2017/0100458 A1 | 4/2017 | Park et al. |

FOREIGN PATENT DOCUMENTS

| CN | 103524623 A | 1/2014 |
| JP | 2008-543887 | 12/2008 |
| JP | 5099832 B2 | 12/2012 |
| JP | 2013-10010 | 1/2013 |
| JP | 5519121 B2 | 6/2014 |
| JP | 2015-502372 | 1/2015 |
| JP | 2017-519505 A | 7/2017 |
| KR | 10-0238551 B1 | 2/2000 |
| KR | 10-2009-033643 A | 4/2009 |
| KR | 10-2012-0089547 A | 8/2012 |
| KR | 10-1420005 B1 | 7/2014 |
| KR | 10-2015-0031210 A | 3/2015 |
| KR | 10-1627917 B1 | 6/2016 |
| KR | 10-1637497 B1 | 7/2016 |
| RU | 2 491 076 C2 | 8/2013 |
| WO | 96/29340 A1 | 9/1996 |
| WO | 0206315 A2 | 1/2002 |
| WO | 2003-050236 A2 | 6/2003 |
| WO | 2006/135982 | 12/2006 |
| WO | 2013/091896 | 6/2013 |
| WO | 2015/194753 A1 | 12/2015 |
| WO | 2016/098936 A1 | 6/2016 |

OTHER PUBLICATIONS

The Merck Manual (<https://www.rnerckmanuals.com/professional/dental-disorders/common-dental-disorders/pulpitis> accessed May 28, 2019).*
Capralogics (<https://capralogics.com/custom-antibody-development-FAQ> Jul. 26, 2011).*
Davari et al. (Dentin Hypersensitivity: Etiology, Diagnosis and Treatment; a literature review; J. Dent (Shiraz) Sep. 2013; 14(3): 136-145).*
NCBI Gen Bank Accession, Jul. 15, 2006; 2 pages; No. AAH35334.
Taduru Srenath et al.; Dentin Sialophosphoprotein Knockout Mouse Teeth Display Widened Predentin Zone and Develop Defective Dentin Mineralization Similar to Human Dentinogenesis Imperfecta Type III; The Journal of Biological Chemistry, Jul. 4, 2003; pp. 24874-24880; vol. 278, No. 27.
Korea Intellectual Property Office, Notice of Rejection of 10-2016-0180408 dated Apr. 14, 2017.
Korea Patent Office, communication dated Apr. 14, 2017 by Korean Patent Office in counterpart Application No. 10-2016-0180408 with English translation.
Australian Patent Office, Communication dated Oct. 15, 2018, issued in counterpart application No. 2017359581.
GenBank Accession No. AJ133799.1, Nov. 14, 2006 available at https://www.ncbi.nlm.nih.gov/nuccore/6453710 (6 pages).
Communication dated Dec. 27, 2018, from Taiwanese Intellectual Property Office in counterpart application No. 106145284.
Lee, et al., "Odontogenic differentiation of human dental pulp stem cells induced by preameloblast-derived factors", Elsevier, Biomaterials, Dec. 2011, vol. 32, Issue 36, pp. 9696-9706. p. 9698, left column, lines 1-3; and p. 9703, left column, lines 7-9, and right column, lines 7-10.
Copine VII, Database GenBank [online], Accession No. AAH35334.1, Jul. 15, 2006 uploaded, [retrieved on May 28, 2019], <https://www.ncbi.nlm.nih.gov/protein/AAH35334. 1/).

(Continued)

*Primary Examiner* — James H Alstrum-Acevedo
*Assistant Examiner* — Tara L Martinez
(74) *Attorney, Agent, or Firm* — Sughrue Mion, PLLC

(57) ABSTRACT

Provided are a novel peptide, a polynucleotide encoding the peptide, an expression vector including the polynucleotide, and a pharmaceutical composition including the peptide, a quasi-drug composition including the peptide, and a health functional food composition including the peptide.

14 Claims, 12 Drawing Sheets

Specification includes a Sequence Listing.

(56) References Cited

OTHER PUBLICATIONS

Predicted: uncharacterized protein L0C10 3233485 isoform X2, Database GenBank [online]. Accession No. XP_007992605. 1, May 14, 2014 uploaded, [retrieved on May 28, 2010], <https.'//www.ncbi.nlm.nih.gov/protein/XP_007992605.1/>.

De Freitas Lima et al., "Antimicrobial Peptide-Based Treatment for Enfofontic Infections—Biotechnological Innovation in Endodontics", Biotechnology Advances, vol. 33, 2015, pp. 203-213.

\* cited by examiner

PEPTIDE FOR PROMOTING REGENERATION OF DENTIN OR DENTAL PULP TISSUE

CROSS-REFERENCE TO RELATED APPLICATION

This is a Divisional Application of U.S. application Ser. No. 15/838,957 filed Dec. 12. 2017, which is a U.S. non-provisional patent application claims priority under 35 U.S.C. § 119 to Korean Patent Application No. 10-2016-0180408, filed on Dec. 27, 2016, in the Korean Intellectual Property Office, the disclosure of which is hereby incorporated by reference in its entirety.

BACKGROUND OF THE INVENTION

1. Field of the Invention

The present invention relates to a novel peptide, and more particularly, to a novel peptide for promoting regeneration of dentin or dental pulp tissues and treating dentin hypersensitivity, a polynucleotide encoding the peptide, an expression vector including the polynucleotide, a pharmaceutical composition for preventing or treating dentin or dental pulp diseases including the peptide, a quasi--drug composition for preventing or improving dentin or dental pulp diseases including the peptide, and a health functional food composition for preventing or improving dentin or dental pulp diseases including the peptide.

2. Description of the Related Art

Dental pulp is a richly innervated and vascularized soft connective tissue that occupies the pulp chamber inside a tooth and extends to the outer surface of the dentin. Disorders occurring in the dental pulp are called dental pulp diseases.

There are many causes of dental pulp diseases, but in most cases, dental pulp diseases are caused by a bacterial infection due to dental caries, or infections in the dental pulp through perforation, odontoclasis, cracks, or periodontal pocket. External wound, abrasion, tooth cracks, or friction or heat from dental equipment may also cause dental pulp diseases. The pulpitis caused by bacterial infection may lead to root apex and periodontal diseases. Dental pulp diseases successively progress to pulp hyperemia, pulpitis, and pulp necrosis. Pulp necrosis may lead to periapical diseases or disorders to the entire tooth, because death of the dental pulp prevents the blood supply to the dental pulp and thus the entire pulp tissue is lost.

For treatment of the pulp or periapical diseases, pulp capping materials and pulp canal filling materials are used, and calcium hydroxides, MTA (Mineral Trioxide Aggregate), Gutta-percha etc., has been generally used. MTA shows therapeutic effects because it has a leakage sealing ability and biocompatibility. However, use of MTA is hampered due to its relatively high cost as a dental repair material and discoloration leading to an esthetic problem. Gutta-percha is relatively low cost and has good flow characteristics. However, it is not a physiologically acceptable method which causes a loss of viability of the pulp. Up to now, conservative treatments for dentin and pulp diseases have problems of the weak or brittle teeth or reinfection.

Therefore, many studies have been actively conducted to develop therapeutic agents capable of effectively treating dentin or pulp diseases. For example, Korean Patent Publication No. 2012-0089547 discloses a composition for forming hard tissues or regenerating dentin or pulp tissues, including ameloblasts, apical bud cells, or cultures thereof as an active ingredient, and Korean Patent Publication No. 2009-0033643 discloses novel tooth stem cells derived from tooth follicles and a method of culturing the same.

The present inventors have made many efforts to develop an agent capable of more effectively treating dentin or dental pulp diseases, and as a result, they developed peptides showing effects of promoting regeneration of dentin or dental pulp tissues and treating dentin hypersensitivity, thereby completing the present invention.

SUMMARY OF THE INVENTION

Embodiments of the present inventive concepts may provide a new peptide for promoting regeneration of dentin or dental pulp tissues and treating dentin hypersensitivity. The peptide of the present invention exhibits excellent effects of promoting regeneration of dentin or dental pulp tissues, and therefore, it may be widely applied to development of a variety of agents for preventing or treating dentin or dental pulp-related diseases.

Embodiments of the present inventive concepts may also provide a polynucleotide encoding the peptide.

Embodiments of the present inventive concepts may also provide an expression vector including the polynucleotide.

Embodiments of the present inventive concepts may also provide a pharmaceutical composition for preventing or treating dentin or dental pulp diseases including the peptide.

Embodiments of the present inventive concepts may also provide a quasi-drug composition for preventing or improving dentin or dental pulp diseases including the peptide.

Embodiments of the present inventive concepts may also provide a health functional food composition for preventing or improving dentin or dental pulp diseases including the peptide.

Embodiments of the present inventive concepts may also provide a method of preventing or treating dentin or dental pulp diseases, the method including administering the composition including the peptide to a subject.

Embodiments of the present inventive concepts may also provide a method of promoting regeneration of dentin or dental pulp tissues, the method including administering the composition including the peptide to a subject.

Embodiments of the present inventive concepts may also provide use of a peptide including an amino acid sequence of the following Formula 1 or a composition including the peptide in promoting regeneration of dentin or dental pulp tissues, in preventing or treating dentin hypersensitivity, and in preventing or treating dentin or dental pulp diseases:

$$K—Y—R1\text{-}R2\text{-}R3\text{-}R4\text{-}R5\text{-}R6\text{-}R7\text{-}R8 \qquad \text{(Formula 1)}$$

wherein R1 is arginine(R), lysine(K) or glutamine(Q);
R2 is arginine(R) or glutamine(Q);
R3, R4, and R5 are arginine(R) or lysine(K), respectively;
R6 is asparagine(N) or serine(S); and
R7 and R8 are lysine(K) or tyrosine,(Y), respectively.

Embodiments of the present inventive concepts may also provide use of a peptide including any one amino acid sequence of SEQ ID NOS: 1 to 96 or a composition including the peptide in promoting regeneration of dentin or dental pulp tissues, in preventing or treating dentin hypersensitivity, and in preventing or treating dentin or dental pulp diseases.

Figure 1A:
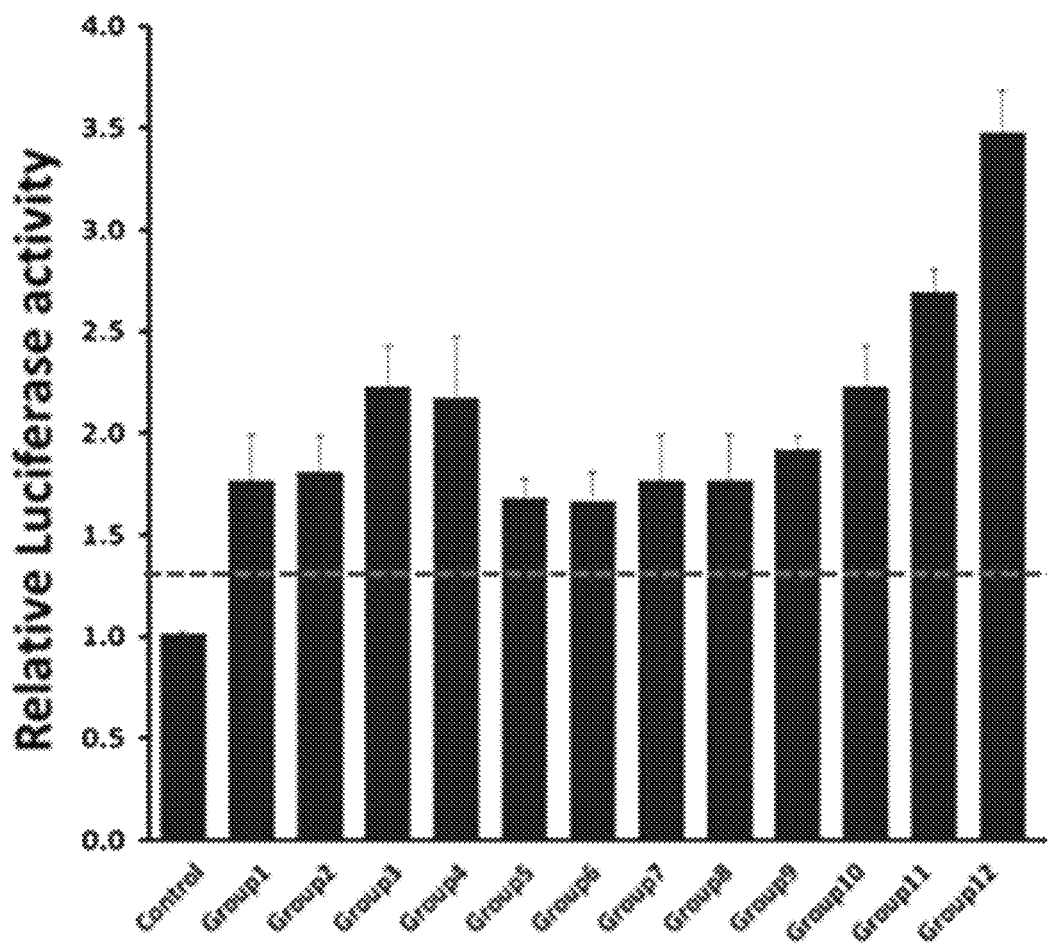
FIG. 1A is a graph showing the results of comparing the effects of the peptides of the respective groups of the present invention on expression of DSPP which is an odontoblast differentiation marker gene.

It should be noted that these figures are intended to illustrate the general characteristics of methods, structures and/or materials utilized in certain example embodiments of the inventive concept and to supplement the written description provided below. These drawings are not necessarily drawn to scale and may not precisely reflect the structural or performance characteristics of any given example embodiment, and should not be interpreted as defining or limiting the range of values or properties encompassed by the example embodiments of the inventive concept.

DETAILED DESCRIPTION OF THE EMBODIMENTS

The present inventors conducted many studies to develop an agent capable of more effectively treating dentin or dental pulp diseases, and as a result, they developed a novel peptide consisting of 10 amino acids.

The newly developed peptide was prepared by substitution of a part of an amino acid sequence of a peptide which may exhibit a therapeutic effect on dentin or dental pulp diseases, and it was confirmed that the newly developed peptide may increase expression levels of Dspp, Dmpl and Nestin genes which are odontoblast differentiation marker genes, thereby showing an effect of promoting dentin regeneration without any cytotoxicity against dental pulp cells.

Further, an implant including the peptide together with dental pulp cells was prepared, and the prepared implant was transplanted into a subcutaneous tissue of an immunocompromised mouse, and after 6 weeks to 12 weeks, the transplanted tissue was analyzed. As a result, it was found that a dentin/pulp-like tissue having the most similar morphology to a dentin/dental pulp tissue in vivo was formed, a production level of collagen was increased, an expression level of DSP which is an odontoblast-specific differentiation marker was increased, whereas an expression level of BSP which is an osteoblast-specific differentiation marker was not markedly increased.

Furthermore, morphology of the transplanted tissue was examined under a scanning electron microscope, and as a result, odontoblast-like cells exhibited a palisade arrangement on the existing dentinal wall, and their cytoplasmic processes, with lengthened nuclei, extended toward existing dentinal tubules.

Effects of the peptide in indirect and direct pulp capping canine models were examined, and as a result, the same physiologic dentin as observed in the natural human tooth dentin was formed by the novel peptide.

Therefore, it can be seen that the peptide of the present invention may exhibit effects of promoting regeneration of dentin or dental pulp and treating dentin hypersensitivity. The peptide of the present invention having these effects has never been reported so far, and it was first developed by the present inventors.

In an aspect to achieve the above-described objects, the present invention provides a peptide for promoting regeneration of dentin or dental pulp and treating dentin or dental pulp diseases, the peptide including an amino acid sequence of the following Formula 1:

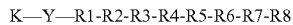  (Formula 1)

wherein R1 is arginine(R), lysine(K) or glutamine(Q);
R2 is arginine(R) or glutamine(Q);
R3, R4, and R5 are arginine(R) or lysine(K), respectively;
R6 is asparagine(N) or serine(S); and
R7 and R8 are lysine(K) or tyrosine(Y), respectively.

The term "dentin", as used herein, is also called dentine, and refers to a yellowish white hard tissue that makes up most of a tooth. The dentin is not exposed to the surface of the tooth, because it is covered by enamel in the tooth crown and cementum in the root. However, dentin exposure may occur at the apical end or the occlusal surface of the tooth crown as the enamel wears with aging. The dentin is a kind of bone tissue, but it is distinguished from a general bone tissue in that the cell bodies of the dentin stay in the dental pulp while their processes extend into the dentinal tubules.

The term "dental pulp tissue", as used herein, is also called "dental pulp", and refers to a soft connective tissue occupying the pulp chamber inside a tooth. Anatomically, the dental pulp has numerous nerves and blood vessels distributed therein, and it extends to the outer surface of the dentin.

The peptide of the present invention is characterized in that it may increase expression levels of Dspp, Dmpl and Nestin genes which are odontoblast differentiation marker genes without cytotoxicity, and when the peptide is transplanted together with dental pulp cells, the dental pulp cells form a dentin/dental pulp-like tissue.

The peptide of the present invention includes peptide variants thereof having a sequence including one or more amino acid residues different from those of the amino acid sequence of the peptide of the present invention, as long as it may promote regeneration of dentin or dental pulp and exhibit a therapeutic effect on dentin or dental pulp diseases.

Amino acid exchanges in proteins and polypeptides, which do not generally alter the molecular activity, are known in the art. The most commonly occurring exchanges are amino acid residues Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, Asp/Gly, in both directions. The peptide may include peptides that have improved structural stability against heat, pH, etc., or improved ability to promote regeneration of dentin or dental pulp due to alteration or modification of the amino acid sequence.

For example, although glutamine which is an acidic amino acid at position 3 of the peptide of SEQ ID NO: 1 of the present invention is substituted with a basic amino acid, lysine or arginine, the effects of the peptide of the present invention may be obtained as it is; although arginine which is a basic amino acid at position 4 or 5 of the peptide of SEQ ID NO: 1 is substituted with an acidic amino acid glutamine or a basic amino acid lysine, the effects of the peptide of the present invention may be obtained as it is; although lysine which is a basic amino acid at position 6, 7 or 9 of the peptide of SEQ ID NO: 1 is substituted with a basic amino acid arginine or an aromatic amino acid tyrosine, the effects of the peptide of the present invention may be obtained as it is; although asparagine which is an acidic amino acid at position 8 of the peptide of SEQ ID NO: 1 is substituted with a neutral amino acid serine, the effects of the peptide of the present invention may be obtained as it is; and although tyrosine which is an aromatic amino acid at position 10 of the peptide of SEQ ID NO: 1 is substituted with a basic amino acid lysine, the effects of the peptide of the present invention may be obtained as it is.

As such, although the acidic amino acids, basic amino acids, or aromatic amino acids constituting the peptide of the present invention are substituted with amino acids having the same properties, or substituted with different acidic amino acids, basic amino acids, neutral amino acids, or aromatic amino acids, respectively, the effects of the peptide of the present invention may be obtained as it is. Therefore, it is apparent that a peptide variant having a sequence including one or more amino acid residues different from those of the amino acid sequence constituting the peptide of the present invention is also included in the scope of the peptide of the present invention.

Further, although arbitrary amino acids are added at the N-terminus or C-terminus of the peptide of the prevention, the effects of the peptide of the present invention may be obtained as it is. Therefore, a peptide prepared by adding arbitrary amino acids at the N-terminus or C-terminus of the peptide of the present invention is also included in the scope of the peptide of the present invention. For example, a peptide prepared by adding 1 to 300 amino acids at the N-terminus or C-terminus of the peptide of the present invention may be exemplified, for another example, a peptide prepared by adding 1 to 100 amino acids at the N-terminus C-terminus of the peptide of the present invention may be exemplified, and for still another example, a peptide prepared by adding 1 to 24 amino acids at the N-terminus or C-terminus of the peptide of the present invention may be exemplified.

The peptide of the present invention may be chemically modified or protected with an organic group at the N-terminus and/or C-terminus, or may be modified by adding amino acids at the peptide terminus in order to protect the peptide from protease in vivo and to increase stability thereof. In particular, since chemically synthesized peptides have charged N-terminus and C-terminus, N-terminal acetylation, N-terminal methylation, or/and C-terminal amidation may be performed, or D-amino acid introduction, peptide bond modification such as $CH_2$—NH, $CH_2$—S, $CH_2$—S=O, $CH_2$—$CH_2$, backbone modification, or side-chain modification may be included in order to remove the charge, but is not limited thereto. Methods of preparing peptidomimetic compounds are well known in the art, for example, referring to a description in Quantitative Drug Design, C A. Ramsden Gd., Choplin Pergamon Press (1992).

The term "backbone modification", as used herein, refers to direct modification of amino acids constituting a peptide backbone with amino acid analogs, in which the backbone (main chain) refers to a main chain- or ring-shaped framework of amino acids constituting a peptide. The amino acid analog refers to an amino acid modified by substitution of hydrogen atoms on the nitrogen or α-carbon of the amino acid backbone.

The term "side-chain modification", as used herein, refers to modification of side-chains of amino acids by using a chemical material, in which the side-chains of amino acids refer to atomic groups branched from a main chain- or ring-shaped framework of amino acids constituting a peptide. Examples of the peptide side-chain modification may include amino group modification such as reductive alkylation; amidation with methyl acetimidate; alkylation with acetic anhydride; carbamylation of amino groups with cyanate; trinitrobenzyation of amino acids with 2,4,6-trinitrobenzene sulfonic acid (TNBS); alkylation of amino groups with succinic anhydride; and pyridoxylation with pyridoxal-3-phosphate followed by reduction with $NaBH_4$.

Further, the peptide of the present invention may be used alone, or in a combination with various carriers approved as a drug, such as an organic solvent. In order to improve stability and efficacy, the peptide of present invention may be also used by including carbohydrates such as glucose, sucrose, or dextran, antioxidants such as ascorbic acid or glutathione, chelating agents, low molecular weight proteins, other stabilizers, etc.

According to an embodiment of the present invention, 96 kinds of peptides corresponding to Formula 1 of the present invention were synthesized, and effects of the synthesized peptides on an expression level of Dspp gene which is an odontoblast differentiation marker gene were examined. As a result, it was confirmed that all mRNA levels of the odontoblast differentiation marker Dspp gene in MDPC-23 cells which were treated with 96 kinds of the peptides were 1.3 times higher than an mRNA level of the Dspp gene which was measured in MDPC-23 cells (control group) which were treated with none of the peptides of the present invention (Tables 13 to 24).

As reported up to now, it is known that as the mRNA level of DSPP is increased, odontoblast differentiation and dentin regeneration are promoted, and therefore, it can be seen that 96 kinds of the peptides showing the effect of increasing the mRNA level of Dspp gene may exhibit the effect of promoting odontoblast differentiation and dentin regeneration (Taduru Sreenath et al THE JOURNAL OF BIOLOGICAL CHEMISTRY, Vol. 278, No. 27, Issue of July 4, pp. 24874-24880. 2003; William T. Butler et al, Connective Tissue Research, 44(Suppl. 1): 171-178, 2003).

In another aspect, the present invention provides a polynucleotide encoding the peptide.

The polynucleotide may he modified by substitution, deletion, or insertion of one or more bases, or a combination thereof. When the nucleotide sequence is prepared by chemical synthesis, a synthetic method widely known in the art, for example, a method described in a literature (Engels and Uhlmann, Angew Chem IntEd Engl., 37:73-127, 1988) may be used and the nucleotide sequence may he synthesized by triester, phosphite, phosphoramidite and H-phosphate methods, PCR and other autoprimer methods, oligonucleotide synthesis on solid supports, etc. For example, the polynucleotide encoding the peptide of the present invention may include a nucleotide sequence of SEQ ID NO: 4.

In still another aspect, the present invention provides an expression vector including the polynucleotide, a transformant including the expression vector, and a method of preparing the peptide by using the transformant.

The term "expression vector", as used herein, refers to a recombinant vector capable of expressing a target peptide in a host cell, and refers to a genetic construct including essential regulatory elements which are operably linked to express a gene insert. The expression vector includes expression regulatory sequences such as an initiation codon, a stop codon, a promoter, an operator, etc. The initiation and stop codons are generally considered as part of a nucleotide sequence encoding a polypeptide and are necessary to be functional in an individual to whom a genetic construct has been administered, and must be in frame with the coding sequence. The promoter of the vector may be constitutive or inducible.

The term "operably linked", as used herein, refers to a functional linkage between a nucleic acid expression control sequence and a nucleotide sequence encoding a target protein or RNA in such a manner as to allow general functions. For example, a promoter may be operably linked to a nucleotide sequence encoding a protein or RNA to influence expression of the coding sequence. The operable linkage to the expression vector may be prepared by using a genetic recombinant technique well known in the art, and site-specific DNA cleavage and ligation may be carried out by using enzymes generally known in the art.

Further, the expression vector may include signal sequences for discharge of the peptide in order to promote isolation of the peptide from a cell culture. Specific initiation signals may also be required for efficient translation of inserted nucleotide sequences. These signals include ATG initiation codon and adjacent sequences. In some cases, exogenous translational control signals, including ATG initiation codon, should be provided. These exogenous translational control signals and initiation codons may be of a variety of origins, both natural and synthetic. The efficiency of expression may be enhanced by introduction of appropriate transcription or translation enhancer elements.

In addition, the expression vector may further include a protein tag that may be optionally removed by endopeptidase in order to facilitate detection of the peptide.

The term "tag", as used herein, refers to a molecule which exhibits a quantifiable activity or characteristic. The tag may include fluorescent molecules including chemical fluorescers such as fluorescein and polypeptide fluorescers such as green fluorescent protein (GFP) or related proteins; and epitope tags such as a tag, a Flag tag, a His tag, a leucine tag, an IgG tag, a streptavidin tag, etc. In particular, if an epitope tag is used, a peptide tag consisting of preferably 6 or more amino acid residues, and more preferably, about 8 to 50 amino acid residues may be used.

In the present invention, the expression vector may include a nucleotide sequence encoding the above-described peptide for promoting regeneration of dentin or dental pulp and treating dentin or dental pulp diseases of the present invention. The vector used herein is not specifically limited, as long as it is able to produce the peptide. Preferably, the vector may be plasmid DNA, phage DNA, etc. More preferably, the vector may be a commercially developed plasmid (pUC18, AIDTSAMRT-AMP, etc.), an *E. coli*-derived plasmid (pYG601BR322, pBR325, pUC118, pUC119, etc.), a *Bacillus subtilis*-derived plasmid (pUB110, pTP5, etc.), a yeast-derived plasmid (YEp13, YEp24, YCp50, etc.), a phage DNA (Charon4A, Charon21A, EMBL3, EMBL4, λgt11, kgt11, λZAP, etc.), an animal virus vector (retrovirus, adenovirus, vaccinia virus, etc.), an insect virus (baculovirus, etc.), or the like. For the expression vector, a host cell most suitable for the intended use is preferably selected and used, because the expression level and modification of protein vary depending on the kind of host cell.

The transformant of the present invention may be prepared by transformation of a host with the expression vector of the present invention, and the transformant may express the polynucleotide in the expression vector, thereby producing the peptide. The transformation may be performed by various methods. The transformation method is not particularly limited, as long as it may produce the peptide. $CaCl_2$ precipitation, a Hanahan method that is an improved $CaCl_2$ precipitation method by using DMSO (dimethyl sulfoxide)

as a reducing agent, electroporation, calcium phosphate precipitation, protoplast fusion, agitation using silicon carbide fiber, *Agrobacterium*-mediated transformation, PEG-mediated transformation, dextran sulfate-, lipofectamine- or desiccation/inhibition-mediated transformation, etc. may be used. The host used in the preparation of the transformant is not particularly limited, as long as it may produce the peptide of the present invention. The host may be bacterial cells such as *E. coli, Streptomyces, Salmonella typhinunium,* etc.; yeast cells such as *Saccharomyces cerevisiae, Schizosaccharomyces pombe,* etc.; fungal cells such as *Pichia pastoris,* etc.; insect cells such as Drosophila, Spodoptera Sf9 cells, etc.; animal cells such as CHO, COS, NSO, 293, Bowes melanoma cells, etc.; and plant cells.

The transformant may be used in a method of producing the peptide for promoting regeneration of dentin or dental pulp and treating dentin hypersensitivity of the present invention. Specifically, the method of producing the peptide for promoting regeneration of dentin or dental pulp and treating dentin or dental pulp diseases of the present invention may include (a) culturing the transformant to obtain a culture; and (b) recovering the peptide of the present invention from the culture.

The term "culturing", as used herein, refers to a method of allowing a microorganism to grow under artificially controlled environmental conditions. In the present invention, the method of culturing the transformant may be performed by a method widely known in the art. Specifically, the culturing is not particularly limited, as long as it may express and produce the peptide for promoting regeneration of dentin or dental pulp and treating dentin or dental pulp diseases of the present invention, and the culturing may be performed by a batch process, a fed-batch process, or a repeated fed batch process.

A medium used in the culturing includes appropriate carbon sources, nitrogen sources, amino acids, vitamins, etc. and should satisfy the requirements of a specific strain in a suitable manner while adjusting temperature, pH, etc. under aerobic conditions. Applicable carbon sources may include, in addition to mixed sugars of glucose and xylose as a main carbon source, sugars and carbohydrates such as sucrose, lactose, fructose, maltose, starch, and cellulose, oils and fats such as soybean oil, sunflower oil, castor oil, coconut oil, etc., fatty acids such as palmitic acid, stearic acid, or linoleic acid, alcohols such as glycerol or ethanol, and organic acids such as acetic acid. These substances may be used alone or in combination. Applicable nitrogen sources may include inorganic nitrogen sources such as ammonia, ammonium sulfate, ammonium chloride, ammonium acetate, ammonium phosphate, ammonium carbonate or ammonium nitrate; amino acids such as glutamic acid, methionine, or glutamine; and organic nitrogen sources such as peptone, NZ-amine, meat extract, yeast extract, malt extract, corn steep liquor, casein hydrolysate, fish meal or digested products thereof, defatted soybean cake or digested products thereof, etc. These nitrogen sources may be used alone or in combination. The medium may include, as phosphorus sources, potassium phosphate monobasic, potassium phosphate dibasic, and corresponding sodium-containing salts. Applicable phosphorus sources may include potassium dihydrogen phosphate, dipotassium hydrogen phosphate, or corresponding sodium-containing salts. In addition, inorganic compounds may include sodium chloride, calcium chloride, iron chloride, magnesium sulfate, iron sulfate, manganese sulfate and calcium carbonate. In addition to the above materials, essential growth materials such as amino acids and vitamins may be used.

Further, appropriate precursors may be used in the culture medium. During culturing, the above-described materials may be appropriately added to the culture in a batch, fed-batch, or continuous manner, but are not limited thereto. The pH of the culture may be adjusted by appropriately using a basic compound such as sodium hydroxide, potassium hydroxide, or ammonia, or an acidic compound such as phosphoric acid or sulfuric acid.

In addition, formation of bubbles may be inhibited by using an antifoaming agent such as fatty acid polyglycol ester. In order to maintain an aerobic state, oxygen or oxygen-containing gas (e.g., air) may be injected into the culture. The temperature of the culture is generally 27° C. to 37° C., preferably 30° C. to 35° C. Culturing is continued until the desired level of the peptide production will be obtained. This is achieved within 10 hours to 100 hours.

In addition, the recovering of the peptide from the culture may be performed by a method known in the art. Specifically, the recovering method is not particularly limited, as long as it may recover the produced peptide. Preferably, a method such as centrifugation, filtration, extraction, spraying, drying, evaporation, precipitation, crystallization, electrophoresis, fractional dissolution (e.g., ammonium sulfate precipitation), chromatography (e.g., ion exchange, affinity, hydrophobic, and size exclusion), etc. may be used.

In still another aspect, the present invention provides a pharmaceutical composition for preventing or treating dentin or dental pulp disease including the peptide.

As described above, when the peptide for promoting regeneration of dentin or dental pulp and treating dentin hypersensitivity of the present invention is transplanted into the body, together with dental pulp cells, formation of dentin/dental pulp-like tissue by the dental pulp cells may be promoted, and when the peptide is applied to the damaged dentin or dental pulp site, the same physiologic dentin as observed in the natural human tooth dentin may be formed. Therefore, the peptide may be used as an active ingredient of the pharmaceutical composition for treating dentin or dental pulp diseases which are caused by damage to dentin or dental pulp.

The peptide included in the pharmaceutical composition may be used in a single form of the peptide or in a polypeptide form of 2 or more repeats of the peptide, and the peptide may he also used in a complex form of a drug having a therapeutic effect on dentin or dental pulp diseases linked at the N-terminus C-terminus of the peptide.

The term "dentin or dental pulp diseases", as used herein, refer to all diseases caused by damaged dental pulp tissue and dentin linked to the dental pulp, due to damage to the dentin and dental pulp tissues.

In the present invention, the dentin or dental pulp diseases are not particularly limited, as long as the peptide of the present invention exhibits the therapeutic effects on the diseases, and the dentin or dental pulp diseases may include, for example, dentin hypersensitivity, pulp hyperemia, pulpitis, pulp degeneration, pulp necrosis, gangrenous pulp, etc.

The term "preventing", as used herein, means all actions by which the occurrence of dentin or dental pulp diseases is restrained or retarded by administration of the pharmaceutical composition for preventing or treating dentin or dental pulp diseases including the peptide of the present invention.

The term "treating", as used herein, means all actions by which dentin or dental pulp diseases are treated by promoting regeneration of dentin or dental pulp by administering the pharmaceutical composition including the peptide of the present invention as an active ingredient to a subject in need of treatment of dentin or dental pulp diseases.

The pharmaceutical composition of the present invention may be prepared in the form of a pharmaceutical composition for treating dentin or dental pulp diseases further including, in addition to the peptide, an appropriate carrier (natural or non-natural carrier), excipient, or diluent commonly used in the preparation of pharmaceutical compositions. Specifically, the pharmaceutical composition may be formulated according to a common method in the form of a sterile injectable solution which may be administered to dentin or dental pulp disease-induced site. In the present invention, the carrier, excipient, and diluent which may be included in the pharmaceutical composition may include lactose, dextrose, sucrose, sorbitol, mannitol, xylitol, erythritol, maltitol, starch acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate, mineral oils, collagen, etc. Upon formulation, commonly used diluents or excipients such as a filler, an extender, a binder, a wetting agent, a disintegrant, a surfactant, etc. may be used. In particular, a sterilized aqueous solution, a non-aqueous solvent, a suspension, an emulsion, a freeze-dried preparation, a suppository, an ointment (e.g., pulp liner, etc.) may be included. As non-aqueous solvents or suspensions, propylene glycol, polyethylene glycol, plant oils such as olive oil, injectable esters such as ethyl oleate, etc. may be used. As a base of the suppositories, witepsol, Macrogol, Tween 61, cacao butter, laurin fat, glycerogelatin, etc. may be used.

A content of the peptide in the pharmaceutical composition of the present invention is not particularly limited, but the peptide may he included in an amount of 0.0001% by weight to 50% by weight, more preferably, 0.01% by weight to 20% by weight, based on the total eight of the final composition.

The pharmaceutical composition of the present invention may be administered in a pharmaceutically effective amount. The term "pharmaceutically effective amount", as used herein, refers to an amount sufficient to treat or prevent diseases, at a reasonable benefit/risk ratio applicable to any medical treatment or prevention. An effective dosage level may be determined depending on factors including severity of the disease, drug activity, a patient's age, body weight, health conditions, sex, sensitivity to the drug, administration time, administration route, and excretion rate of the composition of the present invention, duration of treatment, drugs blended with or co-administered with the composition of the present invention, and other factors known in the medical field. The pharmaceutical composition of the present invention may be administered individually or in combination with a known pharmaceutical composition for treating dentin or pulp diseases. It is important to administer the composition in a minimum amount that may exhibit a maximum effect without causing side effects, in view of all the above-described factors.

An administration dose of the pharmaceutical composition of the present invention may be determined by those skilled in the art, in view of purpose of use, severity of the disease, a patient's age, body weight, sex, and medical history, a kind of a material used as an active ingredient, etc. For example, the pharmaceutical composition of the present invention may be administered at a dose of about 0.1 ng/kg to about 100 mg/kg, and preferably, about 1 ng/kg to about 10 mg/kg per adult, and administration frequency of the composition of the present invention is not particularly limited, but the composition may be administered once a day or several times a day in divided doses. The administration dose does not limit the scope of the present invention in any aspect.

In still another aspect, the present invention provides a method of treating dentin or dental pulp diseases, the method including administering the pharmaceutically effective amount of the pharmaceutical composition to a subject having dentin or dental pulp diseases.

The term "subject," as used herein, may include mammals including rats, livestock, etc. In need of treatment of dentin or dental pulp diseases without limitation.

The pharmaceutical composition for treating dentin or dental pulp diseases of the present invention. may be administered via any general route, as long as the pharmaceutical composition is able to reach a target tissue. The pharmaceutical composition may be administered, but is not particularly limited to, via intraoral administration, intraoral injection, etc., depending on the purpose.

In still another aspect, the present invention provides a quasi-drug composition for preventing or improving dentin or dental pulp diseases including the peptide.

The term "improving", as used herein, means all actions that at least reduce a parameter related to the conditions to be treated, for example, the degree of symptom.

In the present invention, the improving is to be interpreted as all actions by which symptoms of dentin or dental pulp diseases have taken a turn for the better or been modified favorably by promoting regeneration of dentin or dental pulp by administering the pharmaceutical composition including the peptide of the present invention as an active ingredient to a subject in need of treatment of dentin or dental pulp diseases.

The term "quasi-drug", as used herein, refers to an article having a milder action than drugs, among articles being used for the purpose of diagnosis, treatment, improvement, alleviation, handling, or prevention of human or animal diseases. For example, according to Pharmaceutical Affairs Law, the quasi-drugs are those, excluding articles used as drugs, including articles made from fiber or rubber which are used for the purpose of treating or preventing human or animal diseases, articles, other than a tool or a machine, or an analogue thereof, which have a mild action on or have no direct influence on the human body, and articles which are used for the purpose of disinfection or pest control for the prevention of infectious diseases.

In the present invention, a kind or formulation of the quasi-drug composition including the peptide is not particularly limited, but the quasi-drug composition may be, for example, oral antiseptic mouthwashes, oral hygiene products, toothpastes, floss, oral ointments, etc.

In still another aspect, the present invention provides a health functional food composition for preventing or improving dentin or dental pulp diseases including the peptide.

The term "food" as used herein, includes meats, sausages, breads, chocolates, candies, snacks, confectionery, pizzas, ramen noodles, other noodles, gums, dairy products including ice-creams, various soups, beverages, teas, drinks, alcoholic beverages, and vitamin complexes, health functional foods, health foods, etc., and the food includes all foods in the ordinary acceptation of the term.

The term "functional food", as used herein, is the term identical to the food for special health use (FoSHU), and refers to a food having high medical, medicinal effects, which is processed so as to efficiently exhibit the biologically modulating function as well as to supply nutrients. Here, the term "functional" indicates a useful effect for human health, such as regulation of nutrients for the structure and function of the human body, physiological action, etc. The food of the present invention may be prepared according to a method commonly employed in the art, and raw materials and ingredients commonly used in the art may be added upon preparing the food. In addition, a formulation of the food is not limited, as long as the formulation is accepted as a food. The food composition of the present invention may be prepared as a variety of formulations. Since the food is used as raw materials, unlike general drugs, the food composition lacks side effects which may occur when a drug is taken for a long period of time, and may have excellent portability. Therefore, the food of the present invention may be taken as a supplement for enhancing the effects of preventing or improving dentin or dental pulp diseases.

The health food means a food having effects of actively maintaining or promoting health conditions, as compared with general foods, and the health supplement food means a food for supplementing health. If necessary, the health functional food, health food, and health supplement food may be interchangeably used.

Specifically, the health functional food is a food prepared by adding the peptide of the present invention to food materials such as beverages, teas, spices, gums, confectionery, etc. or prepared as a capsule, a powder, a suspension, etc. The health functional food means that it takes a certain effect on health when consumed, but unlike general drugs, the health functional food has an advantage of having no side effects that may occur when a drug is taken for a long time, because it uses a food as a raw material.

Since the food composition of the present invention is routinely ingested, the food composition is expected to show high efficacy on prevention or improvement of dentin or dental pulp diseases, and thus it may be very usefully applied.

The food composition may further include a physiologically acceptable carrier. A kind of the carrier is not particularly limited. Any carrier may be used, as long as it is commonly used in the art.

Further, the food composition may further include additional ingredients that are commonly used in food compositions so as to improve smell, taste, vision, etc. For example, the food composition may include vitamins A, C, D, E, B1, B2, B6, B12, niacin, biotin, folate, pantothenic acid, etc. Additionally, the food composition may also include minerals such as Zn, Fe, Ca, Cr, Mg, Mn, Cu, etc. Additionally, the food composition may also include amino acids such as lysine, tryptophan, cysteine, valine, etc. Additionally, the food composition may also include food additives, such as preservatives (potassium sorbate, sodium benzoate, salicylic acid, sodium dehydroacetate, etc.), disinfectants (bleaching powder, higher bleaching powder, sodium hypochlorite, etc.), antioxidants (butylhydroxyanisole (BHA), butylhydroxytoluene (BHT), etc.), coloring agents (tar color, etc.), color-developing agents (sodium nitrite, etc.), bleaching agents (sodium sulfite), seasonings (monosodium glutamate (MSG), etc.), sweeteners (dulcin, cyclemate, saccharin, sodium, etc.), flavors (vanillin, lactones, etc.), swelling agents (alum, potassium D-bitartrate, etc.), fortifiers, emulsifiers, thickeners (adhesive pastes), film-forming agents, gum base agents, antifoaming agents, solvents, improvers, etc. The additives may be selected and used in an appropriate amount according to the food types.

The peptide of the present invention may be added as it is, or may be used in conjunction with other foods or food ingredients according to a common method, or may be used appropriately according to a common method. Mixing amounts of the active ingredient may be suitably determined depending upon the purpose of use (prophylactic, health or therapeutic treatment). Generally, upon production of a food or a beverage, the food composition of the present invention may be added in an amount of 50 parts by weight or less, specifically 20 parts by weight or less, based on the total weight of the food or the beverage. However, when prolonged intake is intended for the purpose of health and hygiene, the food composition may be included in an amount below the above range. In addition, since there is no safety problem, the active ingredient may be used in an amount above the above range.

The food composition of the present invention may be used as, for example, a health beverage composition, and in this case, the health beverage composition may further include various flavors or natural carbohydrates, as in common beverages. The natural carbohydrates may include monosaccharides such as glucose and fructose; disaccharides such as maltose and sucrose; polysaccharides such as dextrin and cyclodextrin; and sugar alcohols such as xylitol, sorbitol and erythritol. The sweeteners may be natural sweeteners such as thaumatin or a stevia extract; or synthetic sweeteners such as saccaharin or aspartame. The natural carbohydrate may be generally used in an amount of about 0.01 g to 0.04 g, and specifically, about 0.02 g to 0.03 g based on 100 mL of the health beverage composition of the present invention.

In addition, the health beverage composition may include various nutrients, vitamins, minerals, flavors, colorants, pectic acid and salts thereof, alginic acid and salts thereof, organic acids, protective colloidal thickeners, pH modifiers, stabilizers, antiseptics, glycerin, alcohols, carbonating agents, etc. Moreover, the health beverage composition may include the fruit flesh used to prepare natural fruit juices, fruit juice beverages, or vegetable beverages. These ingredients may be used individually or in combination. A proportion of the additives is not critical, but is generally selected from 0.01 parts by weight to 0.1 parts by weight per 100 parts by weight of the health beverage composition of the present invention.

The food composition of the present invention may include the peptide of the present invention in a variety of % by weight, as long as it may exhibit the effect of preventing or improving dentin or dental pulp diseases. Specifically, the peptide of the present invention may be included in an amount of 0.00001% by weight to 100% by weight or 0.01% by weight to 80% by weight, based on the total weight of the food composition, but is not limited thereto.

In still another aspect, the present invention provides a method of preventing or treating dentin or dental pulp diseases, the method including administering the composition including the peptide to a subject.

In still another aspect, the present invention provides a method of promoting regeneration of dentin or dental pulp tissues, the method including administering the composition including the peptide to a subject.

In still another aspect, the present invention provides use of a peptide including an amino acid sequence of the following Formula 1 or a composition including the peptide in promoting regeneration of dentin or dental pulp tissues, in preventing or treating dentin hypersensitivity, and in preventing or treating dentin or dental pulp diseases:

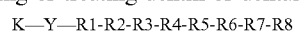 (Formula 1)

wherein R1 is arginine(R), lysine(K) or glutamine(Q);

R2 is arginine(R) or glutamine(Q);

R3, R4, and 1R5 are arginine(R) or lysine(K), respectively;

R6 is asparagine(N) or serine(S); and

R7 and R8 are lysine(K) or tyrosine(Y), respectively.

In still another aspect, the present invention provides use of a peptide including any one amino acid sequence of SEQ ID NOS: 1 to 96 or a composition including the peptide in promoting regeneration of dentin or dental pulp tissues, in preventing or treating dentin hypersensitivity, and in preventing or treating dentin or dental pulp diseases.

Hereinafter, the present invention will be described in more detail with reference to Examples. However, these Examples are for illustrative purposes only, and the scope of the present invention is not intended to be limited by these Examples.

EXAMPLE 1

Synthesis of Peptides for Promoting Generation of Dentin or Dental Pulp Tissues and Treating Dentin Hypersensitivity The present inventors synthesized a peptide (SEQ ID NO: 1) showing the effect of promoting regeneration of dentin or dental pulp tissues by a 9-fluorenylmethyloxycarbonyl (Emoc) method, and they synthesized peptides of respective groups (Tables 1 to 12) by substituting the amino acids of the synthesized peptide.

N-KYQRRKKNKY-C (SEQ ID NO: 1)

First, peptides of Group 1 were synthesized by using the peptide of SEQ ID NO: 1 or by substituting any amino acid at positions 5 to 7 of the peptide of SEQ ID NO: 1 with lysine arginine (Table 1).

TABLE 1

Peptides of Group 1

| SEQ ID NO: | Amino acid sequence(N-C) |
|---|---|
| 1 | KYQRRKKNKY |
| 2 | KYQRRKRNKY |
| 3 | KYQRRRKNKY |
| 4 | KYQRRRRNKY |
| 5 | KYQRKKKNKY |
| 6 | KYQRKRKNKY |
| 7 | KYQRKKRNKY |
| 8 | KYQRKRRNKY |

Next, peptides of Group 2 were synthesized by substituting any amino acid at positions 5 to 7 of the peptide of SEQ ID NO: 1 with lysine or arginine or by substituting an amino acid at position 8 of the peptide of SEQ ID NO: 1 with serine (Table 2).

TABLE 2

Peptides of Group 2

| SEQ ID NO: | Amino acid sequence(N-C) |
|---|---|
| 9 | KYQRRKKSKY |
| 10 | KYQRRKRSKY |
| 11 | KYQRRRKSKY |

TABLE 2-continued

Peptides of Group 2

| SEQ ID NO: | Amino acid sequence(N-C) |
|---|---|
| 12 | KYQRRRRSKY |
| 13 | KYQRKKKSKY |
| 14 | KYQRKRKSKY |
| 15 | KYQRKKRSKY |
| 16 | KYQRKRRSKY |

Next, peptides of Group 3 were synthesized by substituting any amino acid at positions 5 to 7 of the peptide of SEQ ID NO: 1 with lysine or arginine or by substituting an amino acid at position 9 of the peptide of SEQ ID NO: 1 with tyrosine (Table 3).

TABLE 3

Peptides of Group 3

| SEQ ID NO: | Amino acid sequence(N-C) |
|---|---|
| 17 | KYQRRKKNYK |
| 18 | KYQRRKRNYK |
| 19 | KYQRRRKNYK |
| 20 | KYQRRRRNYK |
| 21 | KYQRKKKNYK |
| 22 | KYQRKRKNYK |
| 23 | KYQRKKRNYK |
| 24 | KYQRKRRNYK |

Next, peptides of Group 4 were synthesized by substituting any amino acid at positions 5 to 7 of the peptide of SEQ ID NO: 1 with lysine or arginine, by substituting an amino acid at position 8 of the peptide of SEQ ID NO: 1 with serine, by substituting an amino acid at position 9 of the peptide of SEQ ID NO: 1 with tyrosine, or by substituting an amino acid at position 10 of the peptide of SEQ ID NO: 1 with lysine (Table 4).

TABLE 4

Peptides of Group 4

| SEQ ID NO: | Amino acid sequence(N-C) |
|---|---|
| 25 | KYQRRKKSYK |
| 26 | KYQRRKRSYK |
| 27 | KYQRRRKSYK |
| 28 | KYQRRRRSYK |
| 29 | KYQRKKKSYK |
| 30 | KYQRKRKSYK |
| 31 | KYQRKKRSYK |
| 32 | KYQRKRRSYK |

Next, peptides of Group 5 were synthesized by substituting an amino acid at position 3 of the peptide of SEQ ID NO: 1 with arginine, by substituting an amino acid at position 4 of the peptide of SEQ ID NO: 1 with glutamine, or by substituting any amino acid at positions 5 to 7 of the peptide of SEQ ID NO: 1 with lysine, arginine (Table 5).

TABLE 5

Peptides of Group 5

| SEQ ID NO: | Amino acid sequence(N-C) |
|---|---|
| 33 | KYRQRKKNKY |
| 34 | KYRQRKRNKY |
| 35 | KYRQRRKNKY |
| 36 | KYRQRRRNKY |
| 37 | KYRQKKKNKY |
| 38 | KYRQKRKNKY |
| 39 | KYRQKKRNKY |
| 40 | KYRQKRRNKY |

Next, peptides of Group 6 were synthesized by substituting an amino acid at position 3 of the peptide of SEQ ID NO: 1 with arginine, by substituting an amino acid at position 4 of the peptide of SEQ ID NO: 1 with glutamine, by substituting any amino acid at positions 5 to 7 of the peptide of SEQ ID NO: 1 with lysine or arginine, or by substituting an amino acid at position 8 of the peptide of SEQ ID NO: 1 with serine (Table 6)

TABLE 6

Peptides of Group 6

| SEQ ID NO: | Amino acid sequence(N-C) |
|---|---|
| 41 | KYRQRKKSKY |
| 42 | KYRQRKRSKY |
| 43 | KYRQRRKSKY |
| 44 | KYRQRRRSKY |
| 45 | KYRQKKKSKY |
| 46 | KYRQKRKSKY |
| 47 | KYRQKKRSKY |
| 48 | KYRQKRRSKY |

Next, peptides of Group 7 were synthesized by substituting an amino acid at position 3 of the peptide of SEQ ID NO: 1 with arginine, by substituting an amino acid at position 4 of the peptide of SEQ ID NO: 1 with glutamine, by substituting any amino acid at positions 5 to 7 of the peptide of SEQ ID NO: 1 with lysine or arginine, by substituting an amino acid at position 9 of the peptide of SEQ ID NO: 1 with tyrosine, or by substituting an amino acid at position 10 of the peptide of SEQ ID NO: 1 with lysine (Table 7).

TABLE 7

Peptides of Group 7

| SEQ ID NO: | Amino acid sequence(N-C) |
|---|---|
| 49 | KYRQRKKNYK |
| 50 | KYRQRKRNYK |
| 51 | KYRQRRKNYK |
| 52 | KYRQRRRNYK |
| 53 | KYRQKKKNYK |
| 54 | KYRQKRKNYK |
| 55 | KYRQKKRNYK |
| 56 | KYRQKRRNYK |

Next, peptides of Group 8 were synthesized by substituting an amino acid at position 3 of the peptide of SEQ ID NO: 1 with arginine, by substituting an amino acid at position 4 of the peptide of SEQ ID NO: 1 with glutamine, by substituting any amino acid at positions 5 to 7 of the peptide of SEQ ID NO: 1 with lysine or arginine, by substituting an amino acid at position 8 of the peptide of SEQ ID NO: 1 with serine, by substituting an amino acid at position 9 of the peptide of SEQ ID NO: 1 with tyrosine, or by substituting an amino acid at position 10 of the peptide of SEQ ID NO: 1 with lysine (Table 8).

TABLE 8

Peptides of Group 8

| SEQ ID NO: | Amino acid sequence(N-C) |
|---|---|
| 57 | KYRQRKKSYK |
| 58 | KYRQRKRSYK |
| 59 | KYRQRRKSYK |
| 60 | KYRQRRRSYK |
| 61 | KYRQKKKSYK |
| 62 | KYRQKRKSYK |
| 63 | KYRQKKRSYK |
| 64 | KYRQKRRSYK |

Next, peptides of Group 9 were synthesized by substituting an amino acid at position 3 of the peptide of SEQ ID NO: 1 with lysine, by substituting an amino acid at position 4 of the peptide of SEQ ID NO: 1 with glutamine, or by substituting any amino acid at positions 5 to 7 of the peptide of SEQ ID NO: 1 with lysine or arginine (Table 9).

TABLE 9

Peptides of Group 9

| SEQ ID NO: | Amino acid sequence(N-C) |
|---|---|
| 65 | KYKQRKKNKY |
| 66 | KYKQRKRNKY |
| 67 | KYKQRRKNKY |

TABLE 9-continued

Peptides of Group 9

| SEQ ID NO: | Amino acid sequence(N-C) |
|---|---|
| 68 | KYKQRRRNKY |
| 69 | KYKQKKKNKY |
| 70 | KYKQKRKNKY |
| 71 | KYKQKKRNKY |
| 72 | KYKQKRRNKY |

Next, peptides of Group 10 were synthesized by substituting an amino acid at position 3 of the peptide of SEQ ID NO: 1 with lysine, by substituting an amino acid at position 4 of the peptide of SEQ ID NO: 1 with glutamine, by substituting any amino acid at positions 5 to 7 of the peptide of SEQ ID NO: 1 with lysine or arginine, or by substituting an amino acid at position 8 of the peptide of SEQ ID NO: 1 with serine (Table 10).

TABLE 10

Peptides of Group 10

| SEQ ID NO: | Amino acid sequence(N-C) |
|---|---|
| 73 | KYKQRKKSKY |
| 74 | KYKQRKRSKY |
| 75 | KYKQRRKSKY |
| 76 | KYKQRRRSKY |
| 77 | KYKQKKKSKY |
| 78 | KYKQKRKSKY |
| 79 | KYKQKKRSKY |
| 80 | KYKQKRRSKY |

Next, peptides of Group 11 were synthesized by substituting an amino acid at position 3 of the peptide of SEQ ID NO: 1 with lysine, by substituting an amino acid at position 4 of the peptide of SEQ ID NO: 1 with glutamine, by substituting any amino acid at positions 5 to 7 of the peptide of SEQ ID NO: 1 with lysine or arginine, by substituting an amino acid at position 9 of the peptide of SEQ ID NO: 1 with tyrosine, or by substituting an amino acid at position 10 of the peptide of SEQ ID NO: 1 with lysine (Table 11).

TABLE 11

Peptides of Group 11

| SEQ ID NO: | Amino acid sequence(N-C) |
|---|---|
| 81 | KYKQRKKNYK |
| 82 | KYKQRKRNYK |
| 83 | KYKQRRKNYK |
| 84 | KYKQRRRNYK |
| 85 | KYKQKKKNYK |
| 86 | KYKQKRKNYK |
| 87 | KYKQKKRNYK |
| 88 | KYKQKRRNYK |

Lastly, peptides of Group 12 were synthesized by substituting an amino acid at position 3 of the peptide of SEQ ID NO: 1 with lysine, by substituting an amino acid at position 4 of the peptide of SEQ ID NO: 1 with glutamine, by substituting any amino acid at positions 5 to 7 of the peptide of SEQ ID NO: 1 with lysine or arginine, by substituting an amino acid at position 8 of the peptide of SEQ ID NO: 1 with serine, by substituting an amino acid at position 9 of the peptide of SEQ ID NO: 1 with tyrosine, or by substituting an amino acid at position 10 of the peptide of SEQ ID NO: 1 with lysine (Table 12).

TABLE 12

Peptides of group 12

| SEQ ID NO: | Amino acid sequence(N-C) |
|---|---|
| 89 | KYKQRKKSYK |
| 90 | KYKQRKRSYK |
| 91 | KYKQRRKSYK |
| 92 | KYKQRRRSYK |
| 93 | KYKQKKKSYK |
| 94 | KYKQKRKSYK |
| 95 | KYKQKKRSYK |
| 96 | KYKQKRRSYK |

EXAMPLE 2

Investigation of Efficacy of Peptides for Promoting Regeneration of Dentin or Dental Pulp Tissues and Treating Dentin Hypersensitivity by Using Odontoblasts

EXAMPLE 2-1

Effects of Peptides for Promoting Regeneration of Dentin or Dental Pulp Tissues and Treating Dentin Hypersensitivity on DSPP (Dentin Sialophosphoprotein) Promoter Activity First, MDPC-23 cells which are mouse-derived odontoblasts were cultured in DMED medium supplemented with 10% FBS under conditions of 5% $CO_2$ and 37° C.

Next, the cultured MDPC-23 cells were seeded on a 24-well plate at a density of $5 \times 10^4$ cells per well, and cultured for 24 hours. Then, the cultured cells were transfected with a recombinant vector constructed by introducing a DSPP promoter and a luciferase gene into a pGL3 vector, by using Lipofectamine Plus™ reagent. The transfected MDPC-23 cells were treated with the peptides of Groups 1 to 12 synthesized in Example 1, respectively and cultured for 48 hours. Luciferase activity in each of the transfected MDPC-23 cells was measured, and the calculated mean levels of the respective groups were compared with each other (FIG. 1A). In this regard, transfected MDPC-23 cells which were treated with none of the peptides of the present invention were used as a control group.

FIG. 1A is a graph showing the results of comparing the effects of the peptides of the respective groups of the present invention on expression of DSPP which is an odontoblast differentiation marker gene. As shown in FIG. 1A, overall luciferase activity levels of the respective peptides of the present invention were about 1.3 times higher than that of the control group, but there were differences between groups. It was confirmed that the peptides of Group 12 showed the highest level of luciferase activity, and the peptides of Group 11 showed the next highest level of luciferase activity.

Therefore, it can be seen that the peptides of the present invention exhibit the effect of activating the Dspp promoter.

EXAMPLE 2-2

Figure 1B:
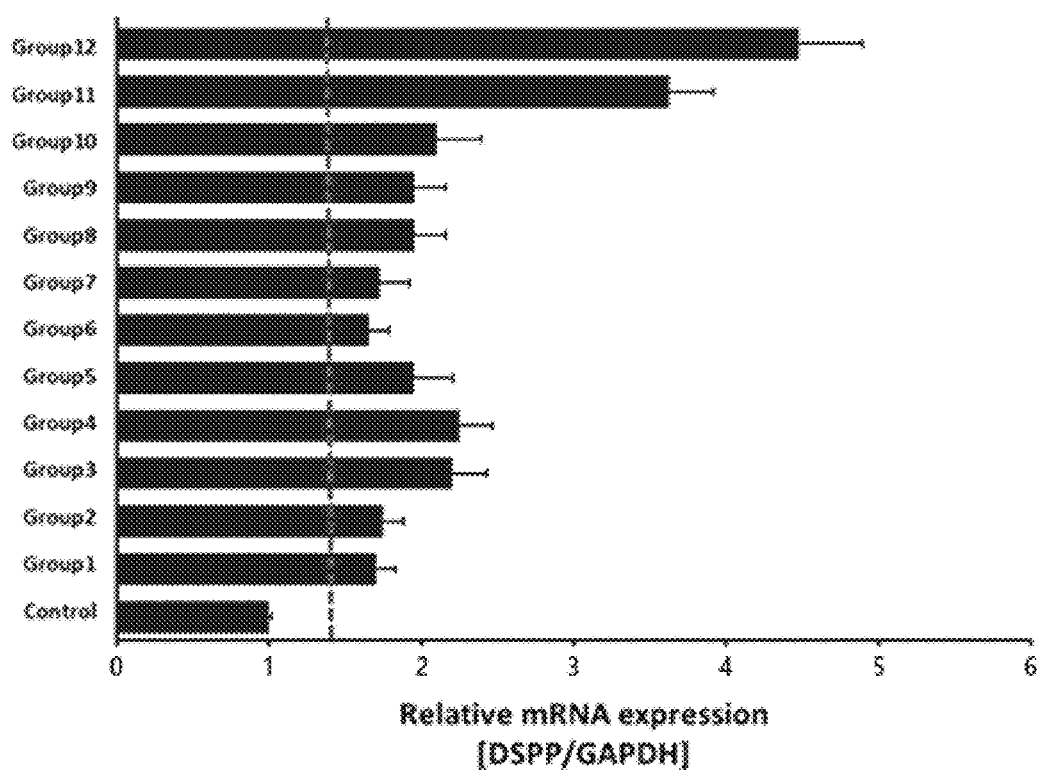
FIG. 1B is a graph showing the results of comparing the expression levels of the odontoblast differentiation marker Dspp gene in MDPC-23 cells treated with the peptides of the present invention.

Effects of Peptides for Promoting Regeneration of Dentin or Dental Pulp Tissues and Treating Dentin or Dental Pulp Diseases on Expression Level of Odontoblast Differentiation Marker DSPP Gene The MDPC-23 cells cultured in Example 2-1 were treated with the peptides of the respective groups which were synthesized in Example 1, and cultured for 48 hours. Then, mRNA levels of an odontoblast differentiation marker Dspp gene expressed in the MDPC-23 cells were measured, and a ratio of the measured Dspp mRNA level relative to a Dspp mRNA level measured in a control group was calculated, respectively (Tables 13 to 24). Further, mean values of the Dspp mRNA levels measured in the peptides of respective groups were compared between the groups (FIG. 1B). In this regard MDPC-23 cells which were treated with none of the peptides of the present invention were used as a control group.

The expression levels of the Dspp gene were measured by RT-PCR and real time PCR analysis: In detail, total RNA was extracted from the MDPC-23 cells with TRIzol reagent. 2 μg of the total RNA, 1 μl of reverse transcriptase, and 0.5 μg oligo (dT) were used to synthesize cDNA. The synthesized cDNA were used in real-time polymerase chain reaction. The real-time polymerase chain reaction was performed on an ABI PRISM 7500 sequence detection system (Applied Biosystems) using the following primers and a SYBR GREEN PCR Master Mix (Takara, Japan). The real-time polymerase chain reaction was performed under conditions of 94° C., 1 min; 95° C., 15 sec 60° C., 34 sec for 40 cycles. Results were analyzed by a comparative cycle threshold (CT) method. In this regard, Gapdh gene was used as an internal control. The experiments were performed in triplicate, and then mean values and standard deviations thereof were taken as measured values.

```
Dspp_R:
                                              (SEQ ID NO: 97)
5'-CTGTTGCTAGTGGTGCTGTT-3'

Dmp1_F:
                                              (SEQ ID NO: 98)
5'-CATTCTCCTTGTGTTCCTTTGGG-3'

Gapdh_F:
                                              (SEQ ID NO: 99)
5'-AGGTCGGTGTGAACGGATTTG-3'

Gapdh_R:
                                              (SEQ ID NO: 100)
5'-TGTAGACCATGTAGTTGAGGTCA-3'
```

TABLE 13

Effects of peptides of Group 1 on mRNA level of Dspp gene

| SEQ ID NO: | mRNA level of Dspp gene | |
|---|---|---|
| | Mean | Standard deviation |
| 1 | 1.754 | 0.132 |
| 2 | 1.646 | 0.092 |
| 3 | 1.464 | 0.221 |
| 4 | 1.855 | 0.102 |
| 5 | 1.639 | 0.057 |
| 6 | 1.746 | 0.091 |
| 7 | 1.864 | 0.132 |
| 8 | 1.639 | 0.032 |

TABLE 14

Effects of peptides of Group 2 on mRNA level of Dspp gene

| SEQ ID NO: | mRNA level of Dspp gene | |
|---|---|---|
| | Mean | Standard deviation |
| 9 | 1.854 | 0.032 |
| 10 | 1.746 | 0.052 |
| 11 | 1.639 | 0.201 |
| 12 | 1.548 | 0.027 |
| 13 | 1.685 | 0.077 |
| 14 | 1.846 | 0.141 |
| 15 | 1.964 | 0.279 |
| 16 | 1.739 | 0.092 |

TABLE 15

Effects of peptides of Group 3 on mRNA level of Dspp gene

| SEQ ID NO: | mRNA level of Dspp gene | |
|---|---|---|
| | Mean | Standard deviation |
| 17 | 2.117 | 0.209 |
| 18 | 2.319 | 0.092 |
| 19 | 1.931 | 0.102 |
| 20 | 2.553 | 0.099 |
| 21 | 1.893 | 0.132 |
| 22 | 2.412 | 0.072 |
| 23 | 2.171 | 0.281 |
| 24 | 2.212 | 0.111 |

TABLE 16

Effects of peptides of Group 4 on mRNA level of Dspp gene

| SEQ ID NO: | mRNA level of Dspp gene | |
|---|---|---|
| | Mean | Standard deviation |
| 25 | 2.371 | 0.089 |
| 26 | 2.193 | 0.052 |
| 27 | 1.993 | 0.202 |
| 28 | 2.453 | 0.192 |
| 29 | 1.883 | 0.101 |

TABLE 16-continued

Effects of peptides of Group 4 on mRNA level of Dspp gene

| SEQ ID NO: | mRNA level of Dspp gene | |
|---|---|---|
| | Mean | Standard deviation |
| 30 | 2.512 | 0.209 |
| 31 | 2.371 | 0.139 |
| 32 | 2.219 | 0.302 |

TABLE 17

Effects of peptides of Group 5 on mRNA level of Dspp gene

| SEQ ID NO: | mRNA level of Dspp gene | |
|---|---|---|
| | Mean | Standard deviation |
| 33 | 1.712 | 0.091 |
| 34 | 1.931 | 0.172 |
| 35 | 1.983 | 0.102 |
| 36 | 2.319 | 0.292 |
| 37 | 1.597 | 0.301 |
| 38 | 2.116 | 0.211 |
| 39 | 1.712 | 0.191 |
| 40 | 2.219 | 0.212 |

TABLE 18

Effects of peptides of Group 6 on mRNA level of Dspp gene

| SEQ ID NO: | mRNA level of Dspp gene | |
|---|---|---|
| | Mean | Standard deviation |
| 41 | 1.546 | 0.091 |
| 42 | 1.586 | 0.103 |
| 43 | 1.669 | 0.095 |
| 44 | 1.793 | 0.203 |
| 45 | 1.532 | 0.310 |
| 46 | 1.887 | 0.077 |
| 47 | 1.697 | 0.009 |
| 48 | 1.558 | 0.201 |

TABLE 19

Effects of peptides of Group 7 on mRNA level of Dspp gene

| SEQ ID NO: | mRNA level of Dspp gene | |
|---|---|---|
| | Mean | Standard deviation |
| 49 | 1.923 | 0.192 |
| 50 | 1.887 | 0.007 |
| 51 | 1.601 | 0.082 |
| 52 | 2.019 | 0.135 |
| 53 | 1.592 | 0.222 |
| 54 | 1.437 | 0.341 |
| 55 | 1.663 | 0.094 |
| 56 | 1.701 | 0.109 |

TABLE 20

Effects of peptides of Group 8 on mRNA level of Dspp gene

| SEQ ID NO: | mRNA level of Dspp gene | |
|---|---|---|
| | Mean | Standard deviation |
| 57 | 2.039 | 0.082 |
| 58 | 1.998 | 0.172 |

TABLE 20-continued

Effects of peptides of Group 8 on mRNA level of Dspp gene

| SEQ ID NO: | mRNA level of Dspp gene | |
|---|---|---|
| | Mean | Standard deviation |
| 59 | 1.792 | 0.007 |
| 60 | 2.107 | 0.201 |
| 61 | 2.301 | 0.019 |
| 62 | 1.672 | 0.308 |
| 63 | 1.769 | 0.085 |
| 64 | 1.967 | 0.039 |

TABLE 21

Effects of peptides of Group 9 on mRNA level of Dspp gene

| SEQ ID NO: | mRNA level of Dspp gene | |
|---|---|---|
| | Mean | Standard deviation |
| 65 | 1.723 | 0.072 |
| 66 | 1.627 | 0.291 |
| 67 | 1.777 | 0.027 |
| 68 | 1.432 | 0.410 |
| 69 | 2.011 | 0.081 |
| 70 | 1.927 | 0.105 |
| 71 | 1.879 | 0.060 |
| 72 | 2.011 | 0.009 |

TABLE 22

Effects of peptides of Group 10 on mRNA level of Dspp gene

| SEQ ID NO: | mRNA level of Dspp gene | |
|---|---|---|
| | Mean | Standard deviation |
| 73 | 2.035 | 0.021 |
| 74 | 2.011 | 0.063 |
| 75 | 1.997 | 0.059 |
| 76 | 2.351 | 0.109 |
| 77 | 1.729 | 0.111 |
| 78 | 2.635 | 0.091 |
| 79 | 2.231 | 0.077 |
| 80 | 1.837 | 0.201 |

TABLE 23

Effects of peptides of Group 11 on mRNA level of Dspp gene

| SEQ ID NO: | mRNA level of Dspp gene | |
|---|---|---|
| | Mean | Standard deviation |
| 81 | 3.092 | 0.152 |
| 82 | 3.361 | 0.098 |
| 83 | 3.572 | 0.209 |
| 84 | 3.702 | 0.301 |
| 85 | 3.670 | 0.088 |
| 86 | 3.705 | 0.137 |
| 87 | 3.888 | 0.072 |
| 88 | 4.021 | 0.301 |

TABLE 24

Effects of peptides of Group 12 on mRNA level of Dspp gene

| SEQ ID NO: | mRNA level of Dspp gene | |
|---|---|---|
| | Mean | Standard deviation |
| 89 | 4.211 | 0.413 |
| 90 | 4.811 | 0.302 |
| 91 | 4.362 | 0.182 |
| 92 | 4.211 | 0.287 |
| 93 | 4.525 | 0.250 |
| 94 | 3.836 | 0.099 |
| 95 | 4.620 | 0.401 |
| 96 | 5.211 | 0.371 |

As shown in Tables 13 to 24, when the peptides of the present invention were treated, overall mRNA levels of the Dspp gene which is an odontoblast differentiation marker were 1.3 times higher than the mRNA level of Dspp gene measured in MDPC-23 cells (control group) treated with none of the peptides of the present invention.

In particular, all peptides of Group 11 showed 3 times higher Dspp mRNA levels and all peptides of Group 12 showed 3.8 times higher Dspp mRNA levels, as compared with the control group.

Moreover, FIG. 1B is a graph showing the results of comparing the expression levels of the odontoblast differentiation marker Dspp gene in the MDPC-23 cells treated with the peptides of the present invention. As shown in FIG. 1B, when the peptides of the present invention were treated, the mRNA levels of the odontoblast differentiation marker Dspp gene were increased, and similar to those of FIG. 1A, the mRNA levels were about 1.3 times higher than the Dspp mRNA level measured in the control group.

EXAMPLE 2-3

Effects of Peptides for Promoting Regeneration of Dentin or Dental Pulp Tissues and Treating Dentin or Dental Pulp Diseases on Expression Levels of Odontoblast Differentiation Marker Genes, Dspp, Dmpl and Nestin The results of Example 2-2 showed that the peptides of the present invention may increase the Dspp mRNA level, and in particular, the peptides of Group 11 and Group 12 may increase the Dspp mRNA level at least three times or higher.

Accordingly, it was examined whether the peptides of Group 11 and Group 12 may increase mRNA levels of other odontoblast differentiation marker genes, Dmpl and Nestin.

Figure 1C:
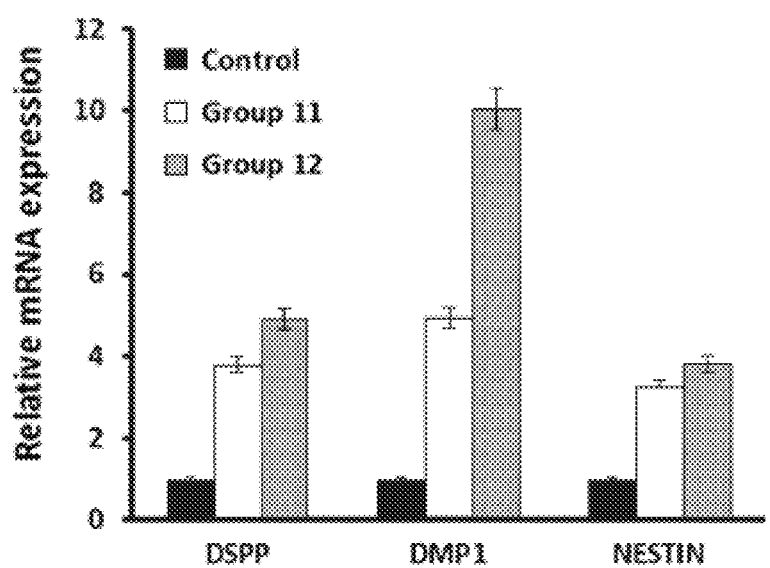
FIG. 1C is a graph showing the results of comparing expression levels of odontoblast differentiation marker genes, Dspp, Dmpl, and Nestin MDPC-23 cells treated with peptides of Group 11 and Group 12 of the present invention.

Briefly, experiments were performed in the same manner as in Example 2-2, except that the following primers were used and the peptides of Group 11 and Group 12 were used as peptides. The effects of the peptides of the present invention on expression levels of Dmpl and Nestin genes were measured, and the calculated mean values were compared between the groups (FIG. 1C). In this regard, MDPC-23 cells which were treated with none of the peptides of the present invention were used as a control group, and the mRNA level of the Dspp gene was used as a comparative group.

```
Dmp1_F:
                                (SEQ ID NO: 101)
    5'-CATTCTCCTTGTGTTCCTTTGGG-3'

Dmp1_R:
                                (SEQ ID NO: 102)
    5'-TGTGGTCACTATTTGCCTGTG-3'

Nestin_F:
                                (SEQ ID NO: 103)
    5'-CCCTGAAGTCGAGGAGCTG-3'

Nestin_R:
                                (SEQ ID NO: 104)
    5'-CTGCTGCACCTCTAAGCGA-3'
```

FIG. 1C is a graph showing the results of comparing the expression levels of the odontoblast differentiation marker genes, Dspp, Dmpl and Nestin in the MDPC-23 cells treated with the peptides of Group 11 and Group 12 of the present invention. As shown in FIG. 1C, when the peptides of the present invention were treated, all mRNA levels of the odontoplast differentiation marker genes, Dspp, Dmpl and Nestin were increased, and there were differences in the creased levels between the genes. The expression levels increased by the peptides of Group 12 were higher than the expression levels increased by the peptides of Group 11.

The above differentiation marker genes are known as genes involved in odontoblast differentiation and dentin mineralization, which infers that the peptides of the present invention may exhibit the effect of promoting dentin regeneration.

EXAMPLE 2-4

Test of Cytotoxicity of Peptides for Promoting Regeneration of Dentin or Dental Pulp Tissues and Treating Dentin or Dental Pulp Diseases in Dental Pulp Cells First, human dental pulp stem cells were separated from wisdom teeth of 10 adults (aged 18-22) at School of Dentistry, Seoul National University. In detail, all experiments were performed after the approval of Institutional Review Board and the informed consent from patients. Wisdom teeth were fractured according to a method of Jung H S et al. (J Mol Histol, (2011)) to expose the dental pulps, and dental pulp tissues were separated with forceps. Each of the separated dental pulp tissues was cut into small pieces with a razor blade, put in a 60-mm dish, covered with a cover slip, and then cultured in a DMEM medium to obtain cultured dental pulp cells.

Figure 1D:
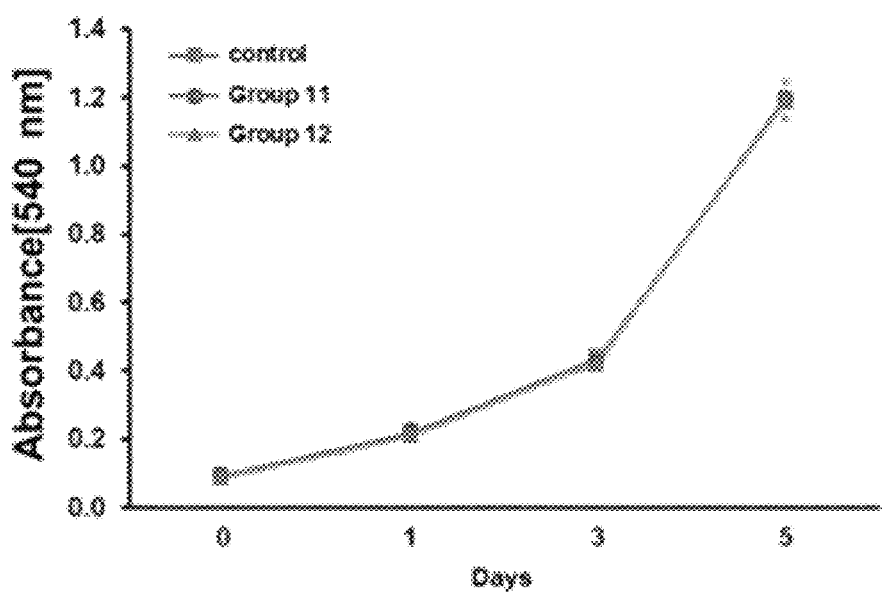
FIG. 1D is a graph showing the results of evaluating cytotoxicity of the peptides of the present invention on dental pulp cells.

Next, the obtained dental pulp cells were seeded on a 96-well plate at a density of $3 \times 10^3$ cells per well, and cultured for 24 hours. Then, the cells were treated with the peptide of Group 11 or 12 at a concentration of 10 μg/ml or 50 μg/ml, and further cultured for 1 day, 3 days, or 5 days. After completion of the culture, the cultured cells were washed with PBS, 20 μl of MTT solution was added thereto, and then allowed to react at 37° C. for 4 hours. After completion of the reaction, the MTT solution was removed, and 100 μl of DMSO was added thereto, and absorbance at 540 nm was measured (FIG. 1D). In this regard, dental pulp cells which were cultured without treatment of the peptides were used as a control group.

FIG. 1D is a graph showing the results of evaluating cytotoxicity of the peptides of the present invention on dental pulp cells. As shown in FIG. 1D, although the peptides of the present invention were treated, the dental pulp cells showed the same level of viability as the control group.

EXAMPLE 3

Effects of Peptides for Promoting Regeneration of Dentin or Dental Pulp Tissues and Treating Dentin or Dental Pulp Diseases on Formation of Dentin Dental Pulp-Like Tissues In Vitro

EXAMPLE 3-1

Figure 2:
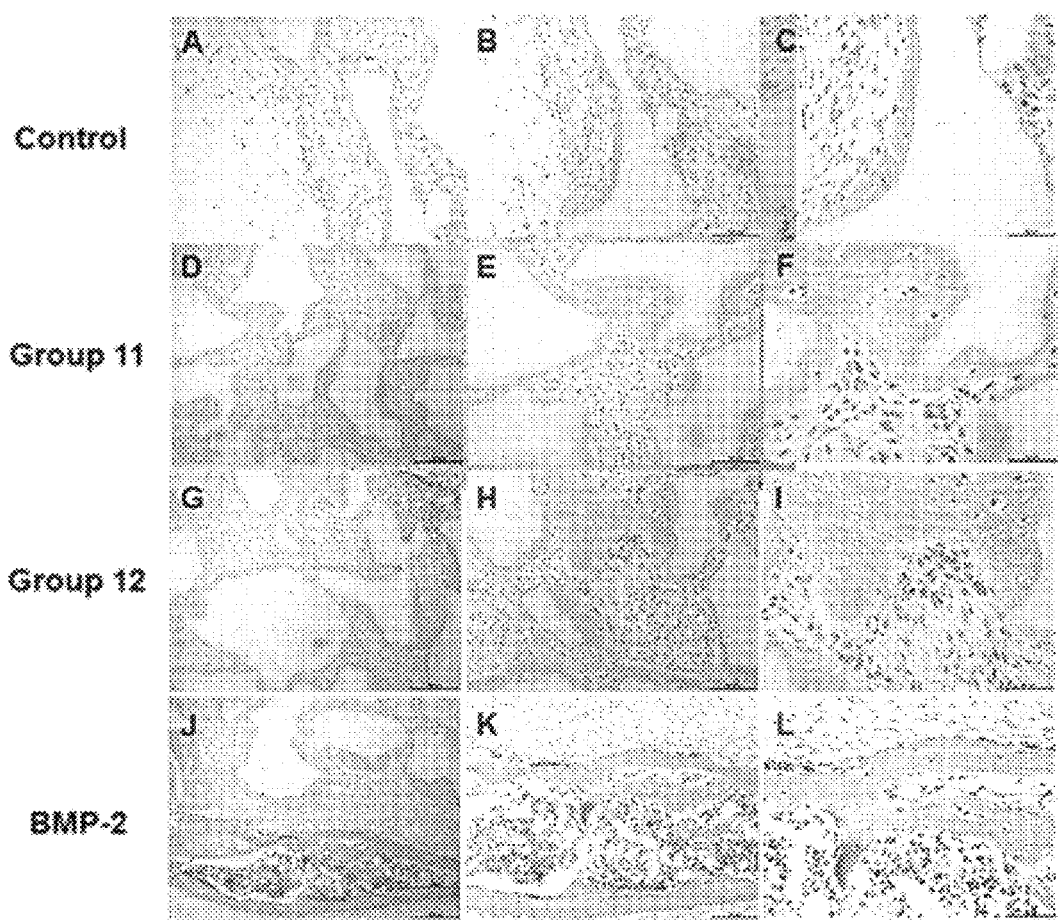
FIG. 2 shows microscopic images of dentin/dental pulp-like tissues which were formed in vivo for 6 weeks after transplantation of implants including dental pulp cells and various components, in which A to C are microscopic images at 6 weeks after transplantation of a control implant including dental pulp cells and HA/TCP only (scale bar: A 200 μm, B 100 μm, C 50 μm); D to F are microscopic images at 6 weeks after transplantation of an implant including dental pulp cells, HA/TCP and the peptide of Group 11 (scale bar: D 200 μm, E 100 μm, F 50 μm); G to I are microscopic images at 6 weeks after transplantation of an implant including dental pulp cells, HA/TCP, and the peptide of Group 12 (scale bar: G 200 μm, H 100 μm, I 50 μm); and J to L are microscopic images at 6 weeks after transplantation of a comparative implant including dental pulp cells, HA/TCP, and rhBMP-2 (scale bar: J 200 μm, K 100 μm, L 50 μm).

Morphological Analysis of Transplanted Tissues Derived from Animals Raised for 6 Weeks 100 mg of a dentin substitute was added to 2×10$^6$ of dental pulp cells, and mixed with 0.5% fibrin gel to prepare an implant. In this regard, hydroxy apatite/tricalcium phosphate (HA/TCP) ceramic powder (Zimmer, USA) was used as the dentin substitute, and the fibrin gel was prepared by including 10 µg of the peptide of Group 11 (SEQ ID NO: 87), the peptide of Group 12 (SEQ ID NO: 96), or 2 µg of BMP-2. The prepared implant was transplanted into the subcutaneous tissues of immunocompromised mice (NIH-bg-nu-xid; Harlan Laboratories, Indianapolis, Ind.), and the mice were raised for 6 weeks. Then, dentin/dental pulp-like tissues formed from the implants were removed. The removed tissues were fixed in 4% paraformaldehyde, decalcified in 10% EDTA (pH 7.4), embedded in paraffin, and stained with hematoxylin-eosin (H-E) (Vector Labs) to evaluate levels of the dentin/dental pulp-like tissues (FIG. 2). In this regard, an implant including none of the peptides of the present invention was used as a control group.

FIG. 2 shows microscopic images of dentin/dental pulp-like tissues which were formed in vivo for 6 weeks after transplantation of the implants including dental pulp cells and various components, in which A to C are microscopic images at 6 weeks after transplantation of a control implant including dental pulp cells and HA/TCP only (scale bar: A 200 µm, B 100 µm, C 50 µm); D to F are microscopic images at 6 weeks after transplantation of an implant including dental pulp cells, HA/TCP and the peptide of Group 11 (scale bar: D 200 µm, E 100 µm, F 50 µm); G to I are microscopic images at 6 weeks after transplantation of an implant including dental pulp cells, HA/TCP, and the peptide of Group 12 (scale bar: G 200 µm, H 100 µm, I 50 µm); and J to L are microscopic images at 6 weeks after transplantation of a comparative implant including dental pulp cells, HA/TCP, and rhBMP-2 (scale bar: J 200 µm, K 100 µm, L 50 µm).

As shown in FIG. 2, when the implant including the peptide of the present invention or not was transplanted (A to I), generation of dentin/dental pulp-like tissue was observed at the periphery of HA/TCP particles. However, when the comparative implant including rhBMP-2 was transplanted (J to L), generation of bone-like mineralized tissue and bone marrow-like tissue was observed at the periphery of HA/TCP particles.

Moreover, dentin/dental pulp-like tissues which were the most similar to the in vivo dentin-dental pulp tissue were generated at a relatively high level upon transplantation of the implants including the peptides of the present invention (D to I), as compared with transplantation of the implants including none of the peptides of the present invention (A to C).

EXAMPLE 3-2

Collagen Staining Analysis of Transplanted Tissues Derived from Animals Raised for 6 Weeks It is known that collagen is the most abundant organic matrix in dentin and bone, and allows mineral deposition to play an important role in dentin regeneration.

Figure 3:
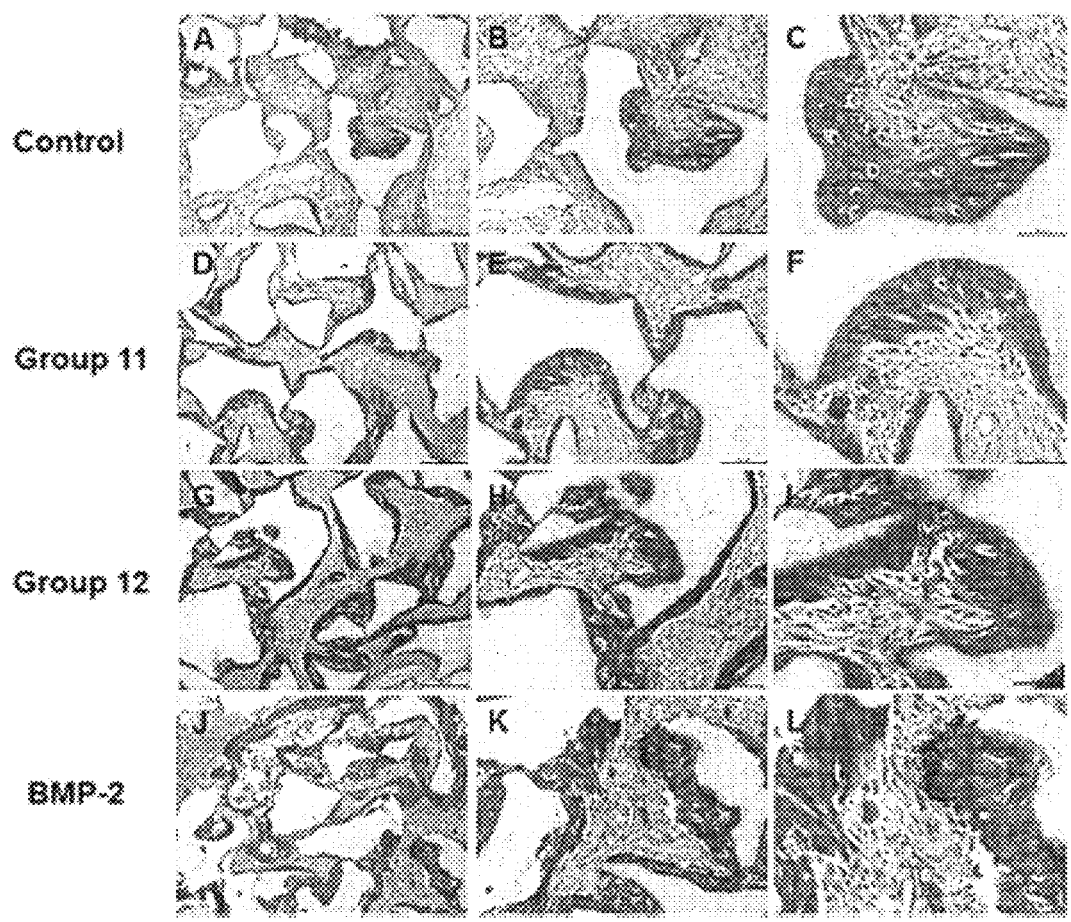
FIG. 3 shows microscopic images of collagen production levels in dentin/dental pulp-like tissues which were formed in vivo for 6 weeks after transplantation of implants including dental pulp cells and various components, in which A to C show the results at 6 weeks after transplantation of a control implant including dental pulp cells and HA/TCP only (scale bar: A 500 μm, B 200 μm, C 50 μm); D to F show the results at 6 weeks after transplantation of an implant including dental pulp cells, HA/TCP, and the peptide of Group 11 (scale bar: D 500 μm, F 200 μm, F 50 μm); G to I show the results at 6 weeks after transplantation of an implant including dental pulp cells, HA/TCP, and the peptide of Group 12 (scale bar: G 500 μm, H 200 μm, I 50 μm); and J to L show the results at 6 weeks after transplantation of a comparative implant including dental pulp cells, HA/TCP, and rhBMP-2 (scale bar: J 500 μm, K 200 μm, L 50 μm).

Accordingly, to examine a collagen production level in each of the tissues removed in Example 3-1, the above tissues were subjected to collagen staining (Masson's Trichrome Staining) by using a Masson's Trichrome Stain Kit (Cat. 25088-100) of Polysciences (FIG. 3). In this regard, a tissue transplanted with an implant including none of the peptides of the present invention was used as a control group.

FIG. 3 shows microscopic images of collagen production levels in the dentin/dental pulp-like tissues which were formed in vivo for 6 weeks after transplantation of the implants including dental pulp cells and various components, in which A to C show the results at 6 weeks after transplantation of a control implant including dental pulp cells and HA/TCP only (scale bar: A 500 µm, B 200 µm, C 50 µm); D to F show the results at 6 weeks after transplantation of an implant including dental pulp cells, HA/TCP, and the peptide of Group 11 (scale bar: D 500 µm, 200 µm, F 50 µm); G to I show the results at 6 weeks after transplantation of an implant including dental pulp cells, HA/TCP, and the peptide of Group 12 (scale bar: G 500 µm, H 200 µm, I 50 µm); and J to L show the results at 6 weeks after transplantation of a comparative implant including dental pulp cells, HA/TCP, and rhBMP-2 (scale bar: J 500 µm, K 200 µm, L 50 µm).

As shown in FIG. 3, transplantation of the implants including the peptides of the present invention showed the increased collagen production levels, as compared with transplantation of the control implant.

EXAMPLE 3-3

Immunostaining Analysis of Transplanted Tissues Derived from Animals Raised for 6 Weeks To evaluate expression levels of DSP which is an odontoblast-specific differentiation marker gene and BSP which is an osteoblast-specific differentiation marker gene in each of the tissues removed in Example 3-1, immunostaining analysis was performed.

Figure 4:
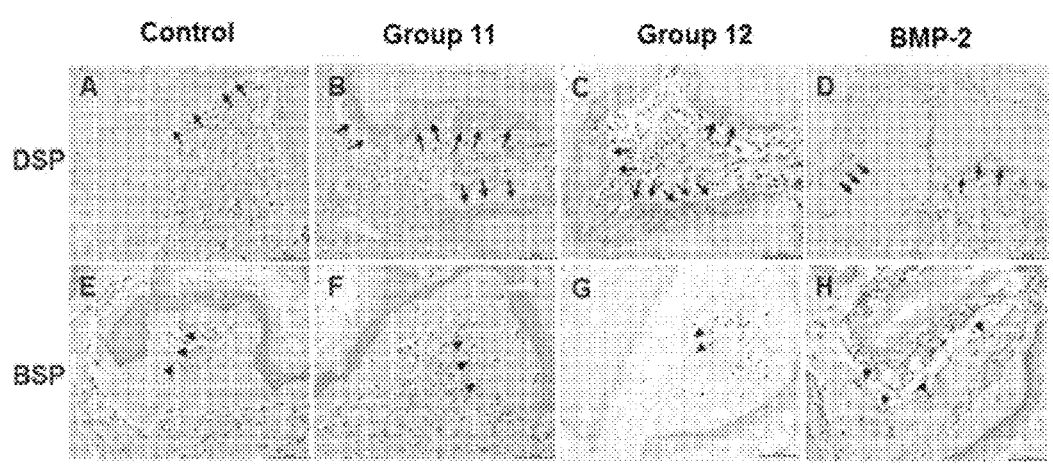
FIG. 4 shows immunostaining images showing the results of evaluating expression levels of DSP which is an odontoblast-specific differentiation marker gene and BSP which is an osteoblast-specific differentiation marker gene in dentin/dental pulp-like tissues which were formed in vitro for 6 weeks after transplantation of implants including dental pulp cells and various components, in which A and E show the results at 6 weeks after transplantation of a control implant including dental pulp cells and HA/TCP only; B and F show the results at 6 weeks after transplantation of an implant including dental pulp cells, HA/TCP, and the peptide of Group 11; C and G show the results at 6 weeks after transplantation of an implant including dental pulp cells, HA/TCP, and the peptide of Group 12; and D and H show the results at 6 weeks after transplantation of a comparative implant including dental pulp cells, HA/TCP and rhBMP-2. Arrows of A, B, C and D indicate DSP-expressing regions in the newly formed dentin-like tissues, and arrowheads of E, C and H indicate BSP-expressing regions in the newly formed bone-like tissues. Scale bar is 50 μm.

Briefly, the removed tissues were fixed in 4% paraformaldehyde, decalcified in 10% EDTA (pH 7.4), embedded in paraffin, and then immunostained with anti-DSP and anti-BSP antibodies at a dilution of 1:150 as primary antibodies, and reacted with biotin-labeled goat anti-rabbit IgG (Vector Labs) as secondary antibodies to determine DSP and BSP levels (FIG. 4). In this regard, the tissue transplanted with an implant including none of the peptides of the present invention was used as a control group.

FIG. 4 shows immunostaining images showing the results of evaluating the expression levels of DSP which is an odontoblast-specific differentiation marker gene and BSP which is an osteoblast-specific differentiation marker gene in the dentin/dental pulp-like tissues which were formed in vivo for 6 weeks after transplantation of the implants including dental pulp cells and various components, in which A and F show the results at 6 weeks after transplantation of a control implant ncluding dental pulp cells and HA/TCP only; B and F show the results at 6 weeks after transplantation of an implant including dental pulp cells, HA/TCP, and the peptide of Group 11; C and G show the results at 6 weeks after transplantation of an implant including dental pulp cells, HA/TCP, and the peptide of Group 12; and D and H show the results at 6 weeks after transplantation of a comparative implant including dental pulp cells, HA/TCP, and rhBMP-2, arrows of A, B, C and D indicate DSP-expressing regions in the newly formed dentin-like tissues, and arrowheads of E, F, G and H indicate BSP-expressing regions in the newly formed bone-like tissues. Scale bar is 50 µm.

As shown in FIG. 4, transplantation of the control implant showed a low DSP expression level in the newly formed dentin/dental pulp-like tissue (A), whereas transplantation of the implant including the peptide of Group 11 or 12 showed a relatively high DSP expression level in the newly formed mineralized tissue (B and C). However, transplantation of the implant including rhBMP2 showed little DSP expression (D).

Further, transplantation of the control implant (E), the implant (F) including the peptide of Group 11, or the implant (G) including the peptide of Group 12 showed a low BSP expression level in the formed mineralized tissue, whereas transplantation of the implant (H) including rhBMP2 showed a relatively very high BSP expression level in the formed mineralized tissue and the osteoblast-like cells entrapped in the mineralized tissue.

EXAMPLE 3-4

Figure 5:
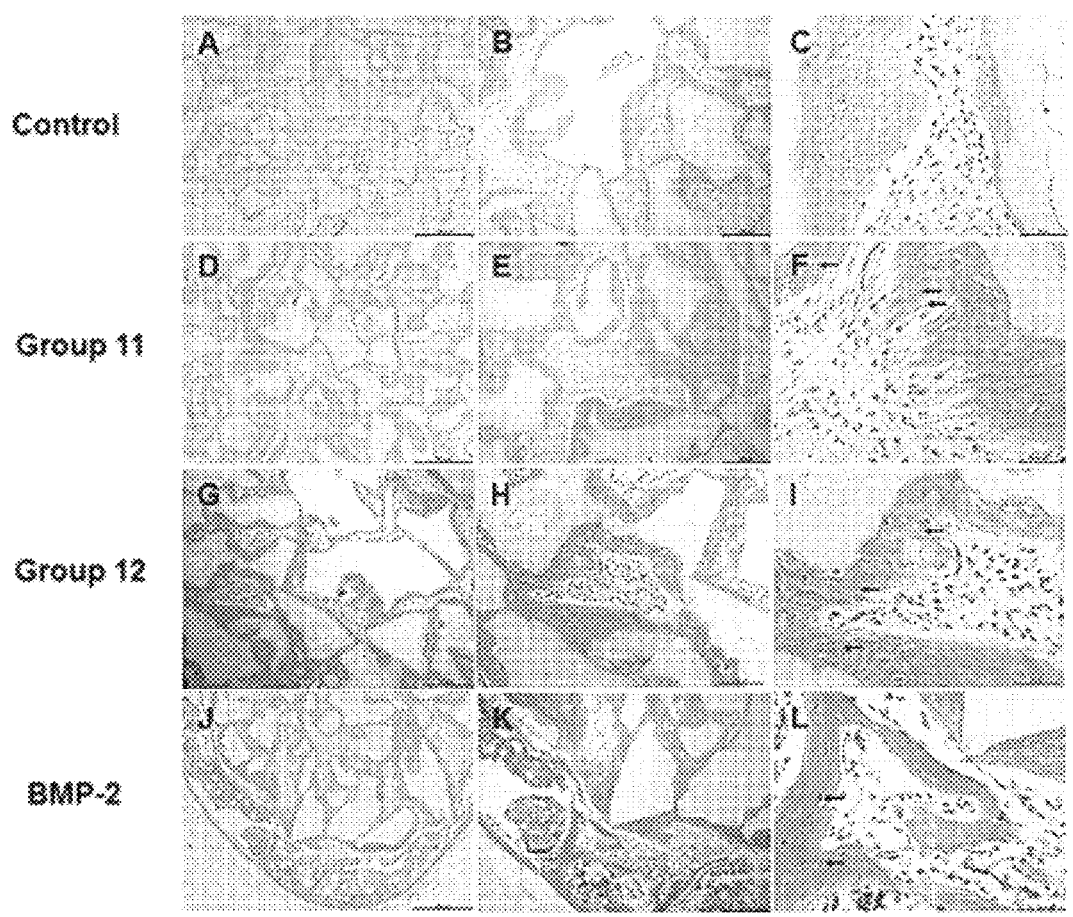
FIG. 5 shows microscopic images of dentin/dental pulp-like tissues which were formed in vivo for 12 weeks after transplantation of implants including dental pulp cells and various components, in which A to C are microscopic images at 12 weeks after transplantation of a control implant including dental pulp cells and HA/TCP only (scale bar: A 500 μm, B 200 μm, C 50 μm); D to F are microscopic images at 12 weeks after transplantation of an implant including dental pulp cells, HA/TCP, and the peptide of Group 11 (scale bar: D 500 μm, E 200 μm, F 50 μm); G to I are microscopic images at 12 weeks after transplantation of an implant including dental pulp cells, HA/TCP, and the peptide of Group 12 (scale bar: G 500 μm, H 200 μm, I 50 μm); and J to L are microscopic images at 12 weeks after transplantation of a comparative implant including dental pulp cells. HA/TCP, and rhBMP-2 (scale bar: J 500 μm, K 200 μm, L 50 μm).

Morphological Analysis of Transplanted Tissues Derived from Animals Raised for 12 Weeks The levels of dentin/dental pulp-like tissues were evaluated in the same manner as in Example 3-1, except implant-transplanted mice were raised for 12 weeks (FIG. 5).

FIG. 5 shows microscopic images of dentin/dental pulp-like tissues which were formed in vivo for 12 weeks after transplantation of the implants including dental pulp cells and various components, in which A to C are microscopic images at 12 weeks after transplantation of a control implant including dental pulp cells and HA/TCP only (scale bar: A 500 µm, B 200 µm, C 50 µm); D to F are microscopic images at 12 weeks after transplantation of an implant including dental pulp cells, HA/TCP, and the peptide of Group 11 (scale bar: D 500 µm, E 200 µm, F 50 µm); G to I are microscopic images at 12 weeks after transplantation of an implant including dental pulp cells, HA/TCP, and the peptide of Group 12 (scale bar: G 500 µm, H 200 µm, I 50 µm); and J to L are microscopic images at 12 weeks after transplantation of a comparative implant including dental pulp cells, HA/TCP, and rhBMP-2 (scale bar: J 500 µm, K 200 µm, L 50 µm).

As shown in FIG. 5, when mice were raised for 12 weeks after transplantation of the implant including the peptide of the present invention or not (A to I), generation of dentin/dental pulp-like tissue and odontoblast processes was observed at the periphery of HA/TCP particles, like in the mice raised for 6 weeks after transplantation. However, when the comparative implant including rhBMP-2 was transplanted (J to L), generation of the bone-like tissue and bone marrow-like tissue having cells entrapped inside the matrix was observed at the periphery of HA/TCP particles.

Moreover, odontoblasts and dentin/dental pulp complexes which were highly similar to those in vivo were generated upon transplantation of the implants including the peptides of the present invention (D to I), as compared with transplantation of the implants including none of the peptides of the present invention (A to C).

EXAMPLE 3-5

Figure 6:
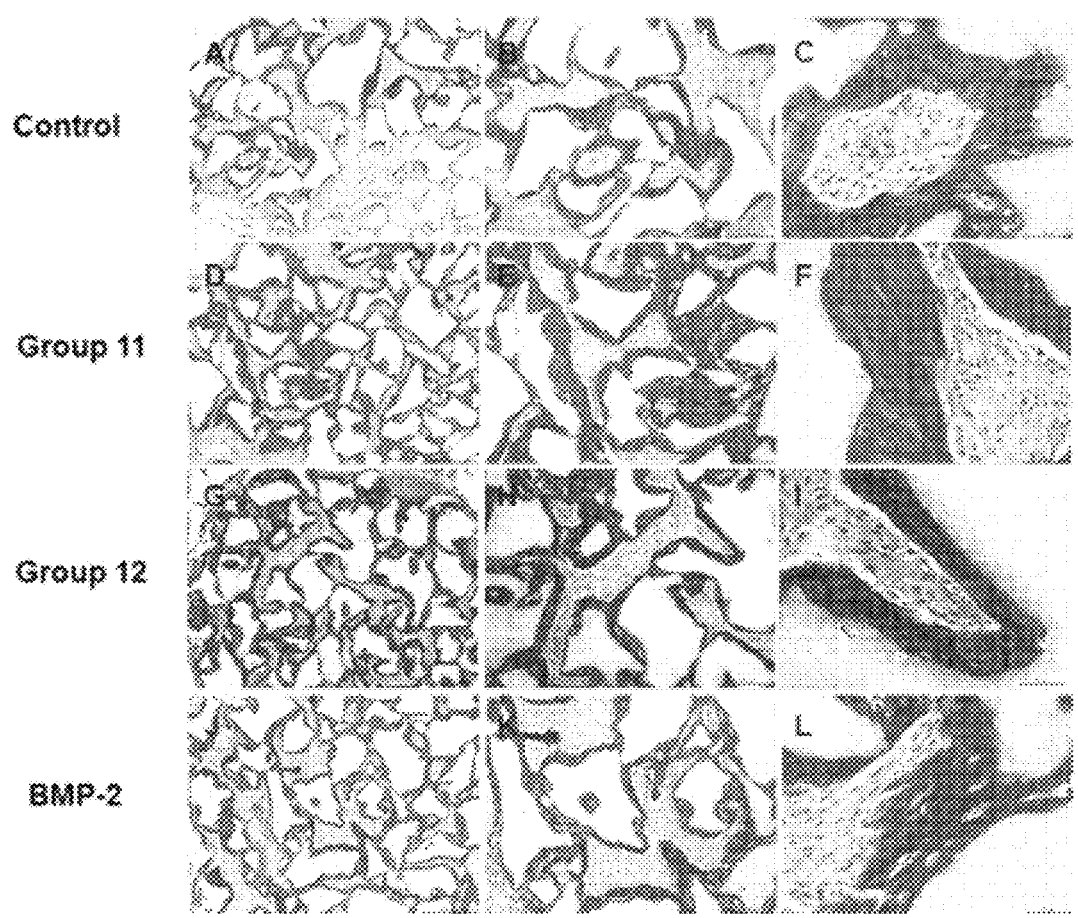
FIG. 6 shows microscopic images of collagen production levels in the dentin/dental pulp-like tissues which were formed in vivo for 12 weeks after transplantation of implants including dental pulp cells and various components, in which A to C show the results at 12 weeks after transplantation of a control implant including dental pulp cells and HA/TCP only (scale bar: A 500 μm, B 200 μm, C 50 μm); D to F show the results at 12 weeks after transplantation of an implant including dental pulp cells, HA/TCP, and the peptide of Group 11 (scale bar: D 500 μm, E 200 μm, F 50 μm); G to I show the results at 12 weeks after transplantation of an implant including dental pulp cells, HA/TCP, and the peptide of Group 12 (scale bar: G 500 μm, H 200 μm, I 50 μm); and J to L show the results at 12 weeks after transplantation of a comparative implant including dental pulp cells, HA/TCP, and rhBMP-2 (scale bar: J 500 μm, K 200 μm, L 50 μm).

Collagen Staining Analysis of Transplanted Tissues Derived from Animals Raised for 12 Weeks In order to examine a collagen production level in each of the tissues removed in Example 3-4, the above tissues were subjected to collagen staining (Masson's Trichrome Staining) by using a Masson's Trichrome Stain Kit (Cat. 25088-100) of Polysciences (FIG. 6). In this regard, a tissue transplanted with an implant including none of the peptides of the present invention was used as a control group.

FIG. 6 shows microscopic images of collagen production levels in the dentin/dental pulp-like tissues which were formed in vivo for 12 weeks after transplantation of the implants including dental pulp cells and various components, in which A to C show the results at 12 weeks after transplantation of a control implant including dental pulp cells and HA/TCP only (scale bar: A 500 µm, B 200 µm, C 50 µm); D to F show the results at 12 weeks after transplantation of an implant including dental pulp cells, HA/TCP, and the peptide of Group 11 (scale bar: D 500 µm, E 200 µm, F 50 µm); G to I show the results at 12 weeks after transplantation of an implant including dental pulp cells, HA/TCP, and the peptide of Group 12 (scale bar: G 500 µm, H 200 µm, I 50 µm); and I to L show the results at 12 weeks after transplantation of a comparative implant including dental pulp cells, HA/TCP, and rhBMP-2 (scale bar: J 500 µm, K 200 µm, L 50 µm).

As shown in FIG. 6, the increased collagen production levels were observed at 12 weeks after transplantation of the implants including the peptides of the present invention, like at 6 weeks after transplantation thereof, as compared with transplantation of the control implant.

EXAMPLE 3-6

Figure 7:
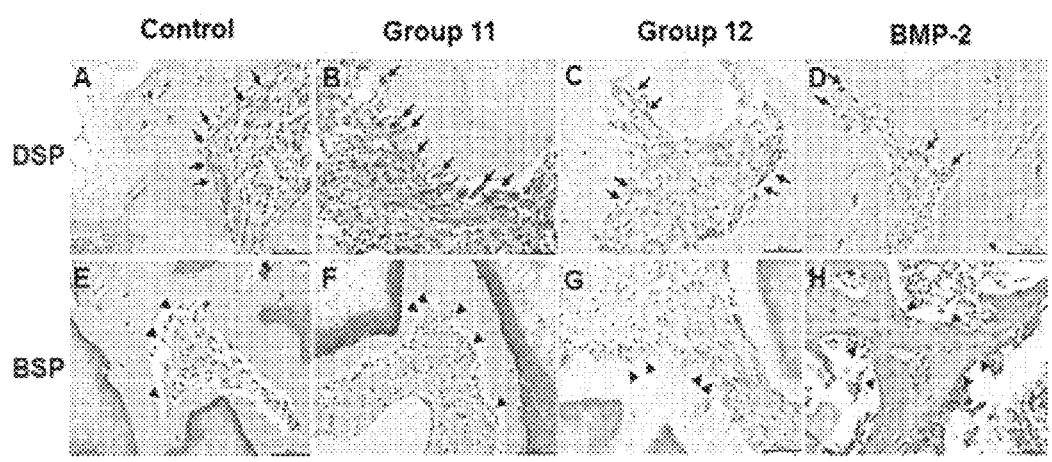
FIG. 7 shows immunostaining images showing the results of evaluating expression levels of DSP which is an odontoblast-specific differentiation marker gene and BSP which is an osteoblast-specific differentiation marker gene in the dentin/dental pulp-like tissues which were formed in vivo for 12 weeks after transplantation of implants including dental pulp cells and various components, in which A and E show the results at 12 weeks after transplantation of a control implant including dental pulp cells and HA/TCP only; B and F show the results at 12 weeks after transplantation of an implant including dental pulp cells, HA/TCP, and the peptide of Group 11; C and G show the results at 12 weeks after transplantation of an implant including dental pulp cells, HA/TCP, and the peptide of Group 12; and D and H show the results at 12 weeks after transplantation of a comparative implant including dental pulp cells, HA/TCP, and rhBMP-2. Arrows of A, B, C and D indicate DSP-expressing regions in the newly formed dentin-like tissues, and arrowheads of E, F, G and H indicate BSP-expressing regions in the newly formed bone-like tissues. Scale bar is 50 μm.

Immunostaining Analysis of Transplanted Tissues Derived from Animals Raised for 12 Weeks Immunostaining analysis was performed in the same manner as in Example 3-3, except that the tissues removed in Example 3-4 were used instead of the tissues removed in Example 3-1 (FIG. 7). In this regard, a tissue transplanted with an implant including none of the peptides of the present invention was used as a control group.

FIG. 7 shows immunostaining images showing the results of evaluating the expression levels of DSP which is an odontoblast-specific differentiation marker gene and BSP which is an osteoblast-specific differentiation marker gene in the dentin/dental pulp-like tissues which were formed in vivo for 12 weeks after transplantation of the implants including dental pulp cells and various components, in which A and E show the results at 12 weeks after transplantation of a control implant including dental pulp cells and HA/TCP only; B and F show the results at 12 weeks after transplantation of an implant including dental pulp cells, HA/TCP, and the peptide of Group 11; C and G show the results at 12 weeks after transplantation of an implant including dental pulp cells, HA/TCP, and the peptide of Group 12; and D and H show the results at 12 weeks after transplantation of a comparative implant including dental pulp cells, HA/TCP, and rhBMP-2, arrows of A, B, C and D indicate DSP-expressing regions in the newly formed dentin-like tissues, and arrowheads of E, F, G and H indicate BSP-expressing regions in the newly formed bone-like tissues. Scale bar is 50 μm.

As shown in FIG. 7, low DSP expression levels were observed in the newly formed dentin/dental pulp-like tissues at 12 weeks after transplantation of the control implant (A) or the implant including rhBMP2 (D), whereas relatively very high DSP expression levels were observed in the newly formed mineralized tissues at 12 weeks after transplantation of the implant (B and C) including the peptide of Group 11 or 12, similar to those at 6 weeks after transplantation.

Further, transplantation of the control implant (E), the implant (F) including the peptide of Group 11, or the implant (G) including the peptide of Group 12 showed a low BSP expression level in the formed mineralized tissue, whereas transplantation of the implant (H) including rhBMP2 showed a relatively very high BSP expression level in the formed mineralized tissue and the osteoblast-like cells entrapped in the mineralized tissue.

Accordingly, it can be seen that the peptides of the present invention exhibit the effect of promoting regeneration of dentin/dental pulp complex.

EXAMPLE 3-7

Analysis of Differentiation of Transplanted Tissue into Odontoblasts

Figure 8:
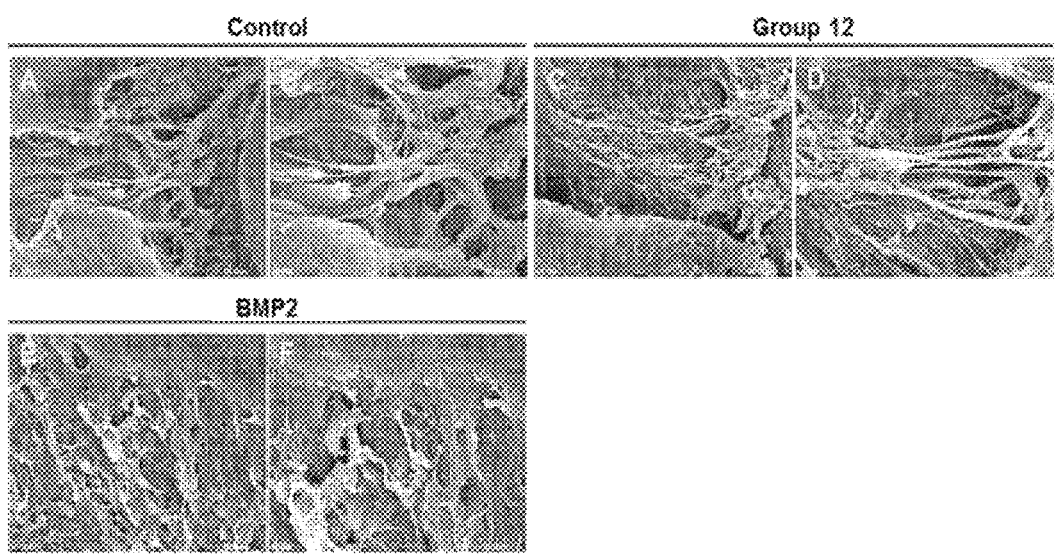
FIG. 8 shows scanning microscopic images of the internal structures of the dentin/dental pulp-like tissues which were formed in vivo at 12 weeks after transplantation of implants including dental pulp cells and various components, in which A and B are the results at 12 weeks after transplantation of a control implant including dental pulp cells and HA/TCP only (scale bar: A 50 μm, B 20 μm); C and D are the results at 12 weeks after transplantation of an implant including dental pulp cells, HA/TCP, and the peptide of Group 12 (SEQ ID NO: 96) (scale bar: C 50 μm, D 20 μm); and E and F are the results at 12 weeks after transplantation of a comparative implant including dental pulp cells, HA/TCP, and rhBMP-2 (scale bar: E 50 μm, F 20 μm).

A scanning electron microscope was used to examine whether the dental pulp cells included in the implant were differentiated into odontoblasts in the tissues removed in Example 3-4 (FIG. 8). In this regard, a tissue transplanted with an implant including none of the peptides of the present invention was used as a control group.

Briefly, each tissue was immersed and fixed in 2.5% glutaraldehyde/0.1 M cacodylate buffer for 30 minutes, and each fixed tissue was immersed and reacted in a cacodylate buffer containing 1% osmium tetroxide for 1 hour. After dehydration of the tissues in ethanol and drying, the dried tissues were coated with gold, and visualized under a scanning electron microscope (S-4700, HITACHI, Tokyo, Japan).

FIG. 8 shows scanning microscopic images of the internal structures of the dentinidental pulp-like tissues which were formed in vivo at 12 weeks after transplantation of the implants including dental pulp cells and various components, in which A and B are the results at 12 weeks after transplantation of a control implant including dental pulp cells and HA/TCP only (scale bar: A 50 μm, B 20 μm); C and D are the results at 12 weeks after transplantation of an implant including dental pulp cells, HA/TCP, and the peptide of Group 12 (SEQ ID NO: 96) (scale bar: C 50 μm, D 20 μm); and E and F are the results at 12 weeks after transplantation of a comparative implant including dental pulp cells, HA/TCP, and rhBMP-2 (scale bar: E 50 μm, F 20 μm).

As shown in FIG. 8, when the control implants (A and B) were transplanted, odontoblast-like cells having odontoblast processes were partially observed at the periphery of the formed hard tissue, and when the implants (C and D) including the peptides of the present invention were transplanted, numerous odontoblast-like cells were observed at the periphery of the formed hard tissue, and odontoblast processes also extended toward the formed hard tissue. However, when the comparative implants (E and F) including rhBMP-2 were transplanted, cuboidal cells attached to the surface of the formed hard tissue were observed, indicating typical characteristics of osteoblasts.

Therefore, it can be seen that the peptides of the present invention more effectively form odontoblasts.

EXAMPLE 4

Effects of Peptides for Promoting Regeneration of Dentin or Dental Pulp Tissues and Treating Dentin Hypersensitivity in Human Tooth Reportedly, the dentinal wall and the empty pulp cavity of a natural tooth provide the specific local environment for the regeneration of dentin/pulp-like tissues by dental pulp cells (Huang G T, et al. (2010) Tissue engineering. Part A 16(2):605-615). Therefore, formation of dentin/pulp-like tissues in root canal spaces was evaluated.

Figure 9:
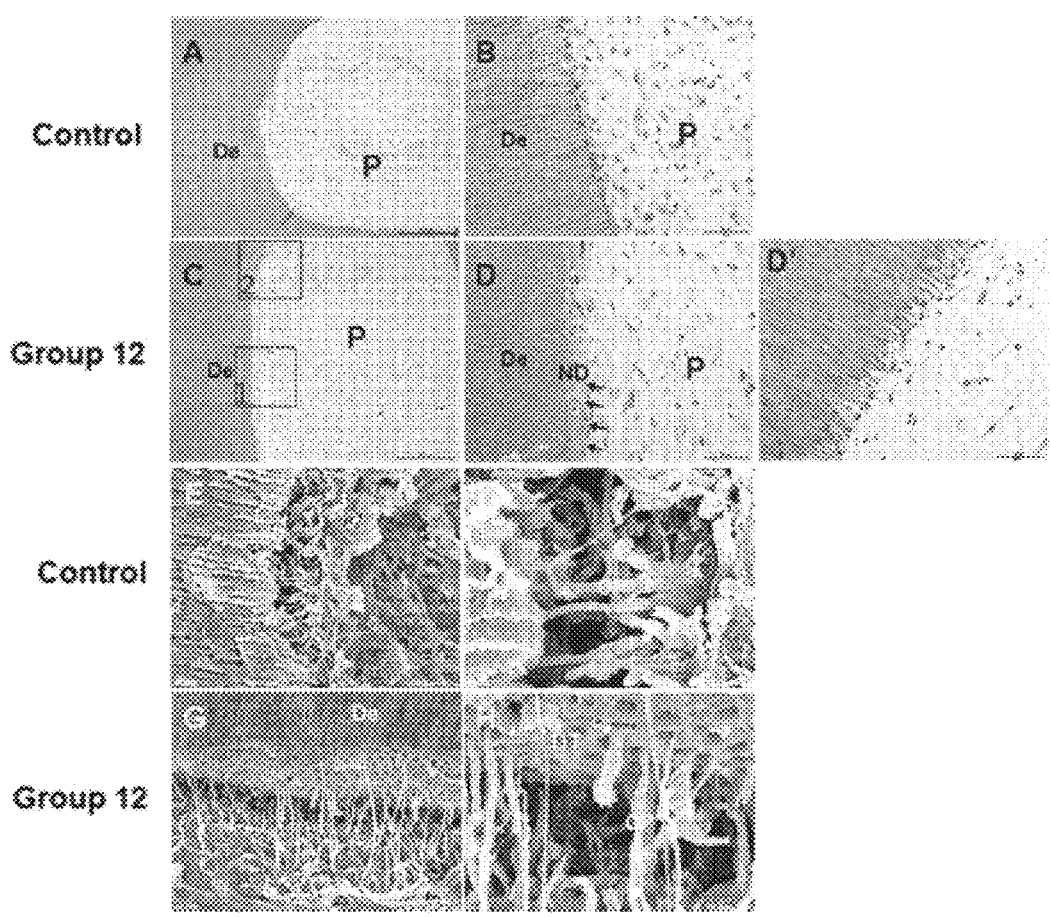
FIG. 9 shows microscopic images and scanning microscopic images showing the results of analyzing odontoblasts/dental pulp-like tissues which were formed after transplantation of implants including the peptides of the present invention into the root canal spaces of the human teeth, in which A and B show the results of staining tissues transplanted with a control implant including dental pulp cells and HA/TCP only (scale bar: A 500 μm, B 50 μm); C, D and D' show the results of staining tissues transplanted with an implant including dental pulp cells, HA/TCP, and the peptide of Group 12 (SEQ ID NO: 96) (scale bar: A 500 μm, B 50 μm); D is magnification of box 1 in C, D' is magnification of box 2 in C (scale bar: C 500 μm, D 50 μm, D' 50 μm); E and F show scanning microscopic images of tissues transplanted with a control implant including dental pulp cells and HA/TCP only (scale bar: E 50 μm, F 10 μm); G and H show scanning microscopic images of tissues transplanted with an implant including dental pulp cells, HA/TCP, and the peptide of Group 12 (SEQ ID NO: 96) (scale bar: G 50 μm, H 10 μm); P indicates regenerated dental pulp, De indicates existing dentinal wall. DT indicates existing dentinal tubules, Od indicates odontoblasts, OP indicates odontoblast processes, and arrows in D indicate regenerated odontoblast-like cells with odontoblast processes.

In detail, among the implants prepared in Example 3-1, a comparative implant or an implant including the peptide of Group 12 (SEQ ID NO: 96) at a concentration of 10 μg/ml was transplanted into the root canal spaces of human teeth for 6 weeks, and dentin dental pulp-like tissues formed in the respective implants were subjected to hematoxylin-eosin (H-E) staining according to the method of Example 3-1, and photographed by a scanning electron microscope according to the method of Example 3-7 (FIG. 9).

FIG. 9 shows microscopic images and scanning microscopic images showing the results of analyzing odontoblasts/dental pulp-like tissues which were formed after transplantation of the implants including the peptides of the present invention into the root canal spaces of the human teeth, in which A and B show the results of staining the tissues transplanted with a control implant including dental pulp cells and HA/TCP only (scale bar: A 500 μm, B 50 μm); C, D and D' show the results of staining the tissues transplanted with an implant including dental pulp cells, HA/TCP and the peptide of Group 12 (SEQ ID NO: 96) (scale bar: A 500 μm, B 50 μm); D is magnification of box 1 in C, D' is magnification of box 2 in C (scale bar: C 500 μm, D 50 μm, D' 50 μm); E and F show scanning microscopic images of the tissues transplanted with the control implant including dental pulp cells, HA/TCP only (scale bar: E 50 μm, F 10 μm); G and H show scanning microscopic images of the tissues transplanted with the implant including dental pulp cells, HA/TCP, and the peptide of Group 12 (SEQ ID NO: 96) (scale bar: G 50 μm, H 10 μm); P indicates the regenerated dental pulp, De indicates existing dentinal wall, DT indicates existing dentinal tubules, Od indicates odontoblasts, OP indicates odontoblast processes, and arrows in D indicate regenerated odontoblast-like cells with odontoblast processes.

As shown in FIG. 9, vascularized pulp-like tissues were formed inside all the root canals which were transplanted with the control implant and the implant including the peptide of Group 12.

However, when the implant including the peptide of Group 12 of the present invention was transplanted, odontoblast-like cells exhibited a palisade arrangement on the existing dentinal wall, and their cytoplasmic processes, with lengthened nuclei, extended toward existing dentinal tubules, and newly formed dentin was observed in the existing dentinal wall (C, D and D').

In particular, as shown in scanning microscopic images (E to H), transplantation of the implants (G and H) including the peptide of Group 12 showed that odontoblast-like cells exhibited a palisade arrangement on the existing dentinal wall, and their cytoplasmic processes, with lengthened nuclei, extended toward existing dentinal tubules, as compared with transplantation of the control implants (E and F).

EXAMPLE 5

Effects of Novel Peptides on Physiologic Dentin (Tertiary Dentin) Formation in Indirect Pulp Capping Canine Model In order to examine effects of the novel peptides on physiologic dentin (tertiary dentin) formation in indirect pulp capping models, their dentin regeneration capabilities were evaluated.

In detail, to establish dentin-damaged canine models by indirect pulp capping, a part of enamel in the cervical part was removed from the premolars of 12-month-old adult dogs by using a dental bur. The dentin was shallowly removed according to the exposure degree of the dentin to form a shallow cavity, thereby establishing a shallow cavity model. The dentin was deeply removed such that the dental pulp was seen through, but not exposed to the outside, thereby establishing a deep cavity model. The models were treated with the control group, the peptide of Group 11, or the peptide of Group 12. 3 weeks later, the adult dogs were euthanized, and teeth were extracted therefrom.

The extracted teeth were fixed in 4% paraformaldehyde for 2.4 hours, washed with PBS (pH 7.4) several times, and then decalcified with 10% formic acid. The decalcified teeth were embedded in paraffin to prepare tissue sections. The tissue sections were stained with hematoxylin/eosin (H&E), and dentin regeneration capabilities were evaluated by histological analysis.

Figure 10:
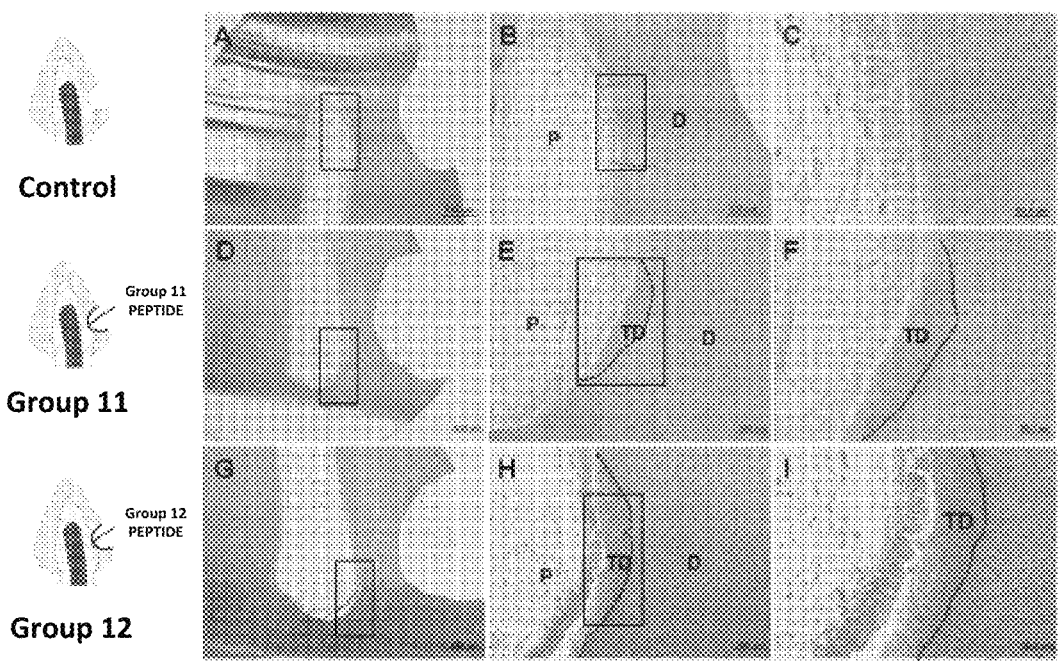
FIG. 10 shows microscopic images of histological analysis of the effects of the novel peptides on physiologic dentin (tertiary dentin) formation in a shallow cavity model among indirect pulp capping canine models, in which A to C are microscopic images showing the result of a control group, in which none of the materials was applied to the inlet of dentinal tubule in the exposed dentin (scale bar: A 500 μm, B 100 μm, C 50 μm); D to F are microscopic images showing the result of applying the peptide of Group 11 (1.5 μg) to the inlet of dentinal tubule in the exposed dentin (scale bar: D 500 μm, E 100 μm, F 50 μm); and G to I are microscopic images showing the result of applying the peptide of Group 12 (1.5 μg) to the inlet of dentinal tubule in the exposed dentin (scale bar: G 500 μm, H 100 μm, I 50 μm). P indicates pulp, D indicates dentin, and TD indicates newly formed physiologic (tertiary) dentin.

FIG. 10 shows microscopic images of histological analysis of the effects of the novel peptides on physiologic dentin (tertiary dentin) formation in the shallow cavity model among the indirect pulp capping canine models, in which A to C are microscopic images showing the result of the control group, in which none of the materials was applied to the inlet of dentinal tubule in the exposed dentin (scale bar: A 500 µm, B 100 µm, C 50 µm); D to F are microscopic images showing the result of applying the peptide of Group 11 (1.5 µg) to the inlet of dentinal tubule in the exposed dentin (scale bar: D 500 µm, E 100 µm, F 50 µm); and G to I are microscopic images showing the result of applying the peptide of Group 12 (1.5 µg) to the inlet of dentinal tubule in the exposed dentin (scale bar: G 500 µm, H 100 µm, I 50 µm). P indicates pulp, D indicates dentin, and TD indicates newly formed physiologic (tertiary) dentin.

In the control group, no change was observed in the damaged dentin (FIG. 10A-C). However, in the groups treated with the peptides of Group 11 (FIG. 10D-F) or Group 12 (FIG. 10G-I), regeneration of physiologic tertiary dentin (TD) which was continuous with the odontoblast processes of the original dentin structure was observed beneath the remaining dentin in the damaged dentin.

Figure 11:
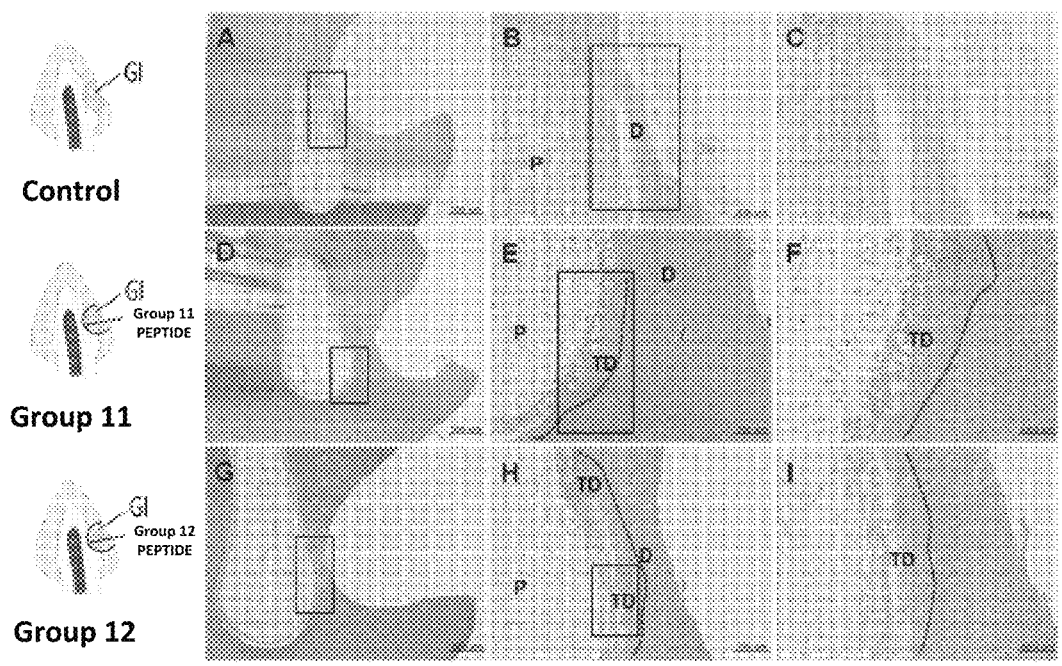
FIG. 11 shows microscopic images of histological analysis of the effects of the novel peptides on physiologic dentin (tertiary dentin) formation in a deep cavity model among indirect pulp capping canine models, in which A to C are microscopic images showing the result of a control group, in which the inlet of dentinal tubule in the exposed dentin was treated with none of the materials and filled with a dental restorative material, GI cement (scale bar: A 500 μm, B 100 μm, C 50 μm); D to F are microscopic images showing the result of filling the inlet of dentinal tubule in the exposed dentin with GI cement after being treated with the peptide of Group 11 (1.5 μg) (scale bar: D 500 μm, E 100 μm, F 50 μm); and G to I are microscopic images showing the results of filling the inlet of dentinal tubule in the exposed dentin with GI cement after being treated with the peptide of Group 12 (1.5 μg) (scale bar: G 500 μm, H 100 μm, I 50 μm). P indicates pulp, D indicates dentin, and TD indicates newly formed physiologic (tertiary) dentin.

FIG. 11 shows microscopic images of histological analysis of the effects of the novel peptides on physiologic dentin (tertiary dentin) formation in the deep cavity model among the indirect pulp capping models, in which A to C are microscopic images showing the result of the control group, in which the inlet of dentinal tubule in the exposed dentin was treated with none of the materials and filled with a dental restorative material, GI cement (Glass Ionomer Cement, Fuji II LC, GC America Inc., Alsip, Ill., USA) (scale bar: A 500 µm, B 100 µm, C 50 µm); D to F are microscopic images showing the result of filling the inlet of dentinal tubule in the exposed dentin with GI cement after being treated with the peptide of Group 11 (1.5 µg) (scale bar: D 500 µm, E 100 µm, F 50 µm); and G to I are microscopic images showing the result of filling the inlet of dentinal tubule in the exposed dentin with GI cement after being treated with the peptide of Group 12 (1.5 µg) (scale bar: G 500 µm, H 100 µm, I 50 µm). P indicates pulp, D indicates dentin, and TD indicates newly formed physiologic (tertiary) dentin.

The deep cavity models showed the similar results to the shallow cavity models. In the control group, in which the damaged dentin lesion was treated with GI cement which is a dental restorative material, no change was observed (FIG. 11A-C). However, in the groups treated with the peptides of Group 11 (FIG. 11D-F) or Group 12 (FIG. 11G-I) together with GI cement, regeneration of physiologic tertiary dentin (TD) which was continuous with the odontoblast processes of the original dentin structure was observed beneath the remaining dentin in the damaged dentin.

EXAMPLE 6

Effects of Novel Peptides on Physiologic Dentin (Tertiary Dentin) Formation in Direct Pulp Capping Canine Model In order to examine effects of the novel peptides on physiologic dentin (tertiary dentin) formation in direct pulp capping models, their dentin regeneration capabilities were evaluated.

In detail, to establish dentin-damaged canine models by direct pulp capping, the enamel and dentin in the cervical part were removed from the premolars of 12-month-old adult dogs by using a dental bur so that the dental pulp was exposed to the outside. The models were treated with the control group, the peptide of Group 11, or the peptide of Group 12. 3 weeks later, the adult dogs were euthanized and teeth were extracted therefrom.

The extracted teeth were fixed in 4% paraformaldehyde for 24 hours, washed with PBS (pH 7.4) several times, and then decalcified with 10% formic acid. The decalcified teeth were embedded in paraffin to prepare tissue sections. The tissue sections were stained with hematoxylin/eosin (H&E), and dentin regeneration capabilities were evaluated by histological analysis.

Figure 12:
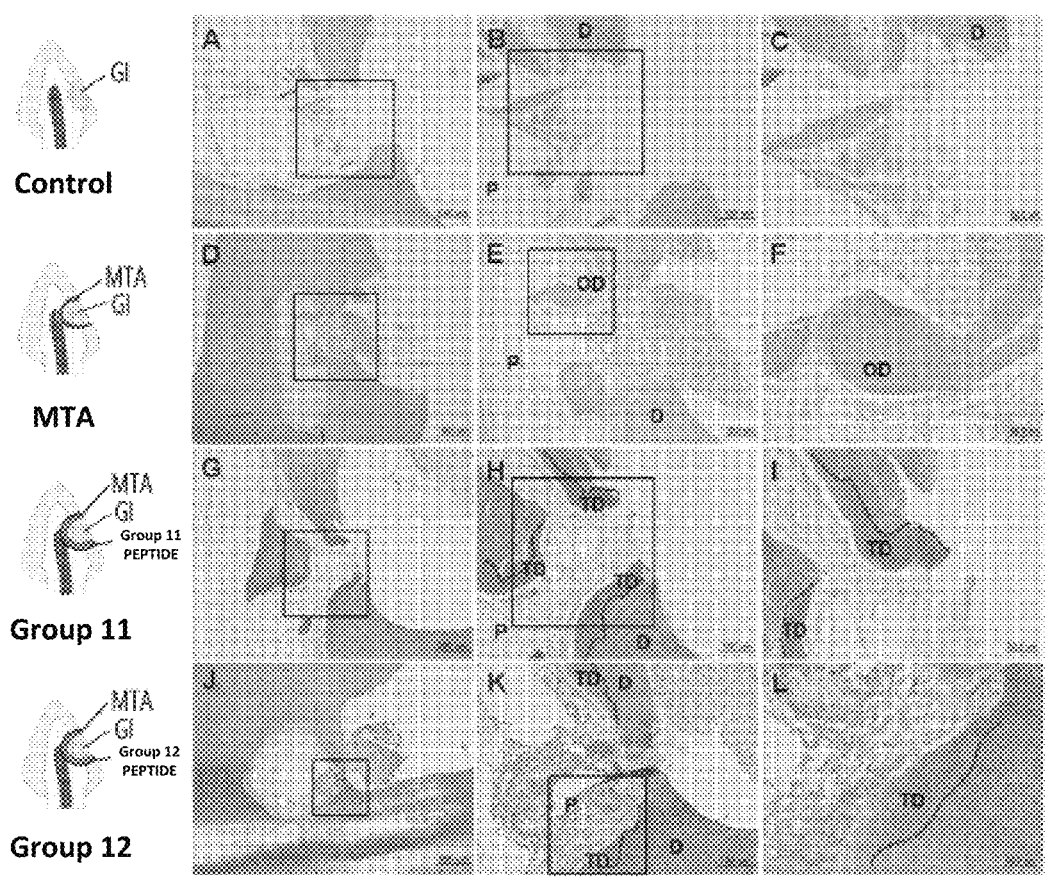
FIG. 12 shows microscopic images of histological analysis of the effects of the novel peptides on physiologic dentin (tertiary dentin) formation in direct pulp capping models, in which A to C are microscopic images showing the result of a control group which was treated with none of the materials and then treated with GI cement (scale bar: A 200 μm, B 100 μm, C 50 μm); D to F are microscopic images showing the result of a positive control group which was treated with none of the materials, sealed with MTA, and then covered with GI cement (scale bar: D 500 μm, E 200 μm, F 50 μm); G to I are microscopic images showing the result of the groups which were treated with the peptide of Group 11 (1.5 μg), sealed with MTA, and then covered with GI cement (scale bar: G 200 μm, H 100 μm, I 50 μm); J to L are microscopic images showing the results of the groups which were treated with the peptide of Group 12 (1.5 μg), sealed with MTA, and then covered with GI cement (scale bar: J 500 μm, K 100 μm, L 50 μm). D indicates dentin, OD indicates osteodentin and TD indicates newly formed physiologic (tertiary) dentin.

FIG. 12 shows microscopic images of histological analysis of the effects of the novel peptides on physiologic dentin (tertiary dentin) formation in the direct pulp capping models, in which A to C are microscopic images showing the results of the control group, in which the exposed dental pulp was treated with none of the materials and then treated with GI cement (scale bar: A 200 µm, B 100 µm, C 50 µm); D to F are microscopic images showing the results of the positive control group, in which the exposed dental pulp was treated with none of the materials, sealed with a dental restorative material, MTA (Mineral trioxide aggregate, ProRoot MTA, Dentsply Tulsa Dental, Tulsa, Okla., USA), and then covered with GI cement (scale bar: D 500 µm, E 200 µm, F 50 µm); G to I are microscopic images showing the results of the groups, in which the exposed dental pulp was treated with the peptide of Group 11 (1.5 µg), sealed with MTA, and then covered with GI cement (scale bar: G 200 µm, H 100 µm, I 50 µm); J to L are microscopic images showing the results of the groups, in which the exposed dental pulp was treated with the peptide of Group 12 (1.5 µg), sealed with MTA, and then covered with GI cement (scale bar: J 500 µm, K 100 μm, L 50 μm). D indicates dentin, OD indicates osteodentin, and TD indicates newly formed physiologic (tertiary) dentin.

In the control group treated with GI cement, no change was observed in the dental pulp of the damaged dentin (FIG. 12A-C). MTA is a dental restorative material widely used in dentin formation and regeneration. However, hard tissues formed by MTA are known to have cells entrapped in the mineralized tissues and to exhibit osteodentin which is similar to bone having no dentinal tubule which is an important component of the dentin. The present results also showed that osteodentin (OD) with cells entrapped in the mineralized tissue along the remaining original dentin on and beneath the exposed pulp was observed in the groups treated with MTA (FIG. 12D-F). However, in the groups treated with MTA and the peptides of Group 11 (FIG. 12G-I) or Group 12 (FIG. 123-L), new physiologic dentin (TD) which was continuous with the odontoblast processes of the original dentin was formed along the remaining original dentin on and beneath the exposed pulp.

The results of Examples taken together, it can be seen that the peptides of the present invention increase expression levels of Dspp, Dmp1 and Nestin genes which are odontoblast-specific differentiation marker genes, and promote formation of odontoblasts when the peptides are transplanted, together with dental pulp cells, into the body, and in particular, the dental pulp cells promote formation of dentinidental pulp-like tissue when the peptides are transplanted into root canal spaces. It can he also seen that the same physiologic dentin as observed in he natural human tooth dentin is formed by the novel peptides.

Accordingly, it can be seen that the peptides of be present invention may be used in the treatment of dentin or dental pulp diseases.

This work was supported by the Technology Innovation Program (10078369, "Development of original technology for the treatment of tooth hypersensitivity using dentin regenerating functional peptides") funded By the Ministry of Trade, Industry & Energy(MOTIE, Korea)"

What is claimed is:

1. A method of treating dentin hypersensitivity and/or promoting regeneration of dentin or dental pulp tissues of a subject in need thereof, comprising administering to the subject a composition comprising one or more of the following (i)-(iii):
   (i) a peptide comprising an amino acid sequence of the following Formula 1:

K—Y—R1-R2-R3-R4-R5-R6-R7-R8        (Formula 1)

wherein R1 is arginine(R), lysine(K), or glutamine(Q);
   R2 is arginine(R) or glutamine(Q);
   R3, R4, and R5 are arginine(R) or lysine(K), respectively:
   R6 is asparagine(N) or serine(S); and
   R7 and R8 are lysine(K) or tyrosine(Y), respectively,
   (ii) a polypeptide compound prepared by linking repeats of the peptide (i), and
   (iii) a complex of the peptide (i) linked to a drug having a therapeutic effect on dentin or dental pulp diseases.

2. The method of claim 1, wherein the peptide of-(i) comprises any one of the amino acid sequences of SEQ ID NOS: 1 to 96.

3. The method of claim 2, wherein the peptide (i) has a modification selected from the group consisting of N- or C-terminal acetylation, amidation, or methylation; D-amino acid introduction; peptide bond modification selected from the group consisting of $CH_2$—NH, $CH_2$—S, $CH_2$—S=O, $CH_2$—$CH_2$; backbone modification; and side-chain modification.

4. The method of claim 2, wherein the composition is a pharmaceutical composition and further comprises a pharmaceutically acceptable carrier, excipient, or diluent.

5. The method of claim 2, wherein the composition is a food.

6. The method of claim 2, wherein the composition is an oral antiseptic mouthwash, oral hygiene product, toothpaste, dental floss, or oral ointment.

7. The method of claim 2, wherein the composition comprises the peptide of (i) and the polypeptide of (ii).

8. The method of claim 2, wherein the composition comprises the peptide of (i) and the complex of (iii).

9. The method of claim 1, wherein the peptide (i) has a modification selected from the group consisting of N- or C-terminal acetylation, amidation, or methylation; D-amino acid introduction; peptide bond modification selected from the group consisting of $CH_2$—NH, $CH_2$—S, $CH_2$—S=O, $CH_2$—$CH_2$; backbone modification; and side-chain modification.

10. The method of claim 1, wherein the composition is a pharmaceutical composition and further comprises a pharmaceutically acceptable carrier, excipient, or diluent.

11. The method of claim 1, wherein the composition is a food.

12. The method of claim 1, wherein the composition is an oral antiseptic mouthwash, oral hygiene product, toothpaste, dental floss, or oral ointment.

13. The method of claim 1, wherein the composition comprises the peptide of (i) and the polypeptide of (ii).

14. The method of claim 1, wherein the composition comprises the peptide of (i) and the complex of (iii).

* * * * *

SEQUENCE LISTING

```
<160> NUMBER OF SEQ ID NOS: 104

<210> SEQ ID NO 1
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 1

Lys Tyr Gln Arg Arg Lys Lys Asn Lys Tyr
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 2

Lys Tyr Gln Arg Arg Lys Arg Asn Lys Tyr
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 3

Lys Tyr Gln Arg Arg Arg Lys Asn Lys Tyr
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 4

Lys Tyr Gln Arg Arg Arg Arg Asn Lys Tyr
1               5                   10
```

```
<210> SEQ ID NO 5
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 5

Lys Tyr Gln Arg Lys Lys Lys Asn Lys Tyr
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 6

Lys Tyr Gln Arg Lys Arg Lys Asn Lys Tyr
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 7

Lys Tyr Gln Arg Lys Lys Arg Asn Lys Tyr
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 8

Lys Tyr Gln Arg Lys Arg Arg Asn Lys Tyr
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 9

Lys Tyr Gln Arg Arg Lys Lys Ser Lys Tyr
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 10

Lys Tyr Gln Arg Arg Lys Arg Ser Lys Tyr
1               5                   10
```

<210> SEQ ID NO 11
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 11

Lys Tyr Gln Arg Arg Arg Lys Ser Lys Tyr
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 12

Lys Tyr Gln Arg Arg Arg Arg Ser Lys Tyr
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 13

Lys Tyr Gln Arg Lys Lys Lys Ser Lys Tyr
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 14

Lys Tyr Gln Arg Lys Arg Lys Ser Lys Tyr
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 15

Lys Tyr Gln Arg Lys Lys Arg Ser Lys Tyr
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 16

Lys Tyr Gln Arg Lys Arg Arg Ser Lys Tyr
1               5                   10

```
<210> SEQ ID NO 17
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 17

Lys Tyr Gln Arg Arg Lys Lys Asn Tyr Lys
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 18

Lys Tyr Gln Arg Arg Lys Arg Asn Tyr Lys
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 19

Lys Tyr Gln Arg Arg Arg Lys Asn Tyr Lys
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 20

Lys Tyr Gln Arg Arg Arg Arg Asn Tyr Lys
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 21

Lys Tyr Gln Arg Lys Lys Lys Asn Tyr Lys
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 22

Lys Tyr Gln Arg Lys Arg Lys Asn Tyr Lys
1               5                   10

<210> SEQ ID NO 23
```

```
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 23

Lys Tyr Gln Arg Lys Lys Arg Asn Tyr Lys
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 24

Lys Tyr Gln Arg Lys Arg Arg Asn Tyr Lys
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 25

Lys Tyr Gln Arg Arg Lys Lys Ser Tyr Lys
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 26

Lys Tyr Gln Arg Arg Lys Arg Ser Tyr Lys
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 27

Lys Tyr Gln Arg Arg Arg Lys Ser Tyr Lys
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 28

Lys Tyr Gln Arg Arg Arg Arg Ser Tyr Lys
1               5                   10

<210> SEQ ID NO 29
<211> LENGTH: 10
```

```
<212> TYPE: PRT
<213> ORGANISM: Artificial Sequence
<220> FEATURE:
<223> OTHER INFORMATION: Synthetic construct of novel peptide

<400> SEQUENCE: 29

Lys Tyr Gln Arg Lys Lys Lys Ser Tyr Lys
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 30

Lys Tyr Gln Arg Lys Arg Lys Ser Tyr Lys
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 31

Lys Tyr Gln Arg Lys Lys Arg Ser Tyr Lys
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 32

Lys Tyr Gln Arg Lys Arg Arg Ser Tyr Lys
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 33

Lys Tyr Arg Gln Arg Lys Lys Asn Lys Tyr
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 34

Lys Tyr Arg Gln Arg Lys Arg Asn Lys Tyr
1               5                   10

<210> SEQ ID NO 35
<211> LENGTH: 10
<212> TYPE: PRT
```

```
<213> ORGANISM: Artificial Sequence
<220> FEATURE:
<223> OTHER INFORMATION: Synthetic construct of novel peptide

<400> SEQUENCE: 35

Lys Tyr Arg Gln Arg Arg Lys Asn Lys Tyr
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 36

Lys Tyr Arg Gln Arg Arg Arg Asn Lys Tyr
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 37

Lys Tyr Arg Gln Lys Lys Lys Asn Lys Tyr
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 38

Lys Tyr Arg Gln Lys Arg Lys Asn Lys Tyr
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 39

Lys Tyr Arg Gln Lys Lys Arg Asn Lys Tyr
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 40

Lys Tyr Arg Gln Lys Arg Arg Asn Lys Tyr
1               5                   10

<210> SEQ ID NO 41
<211> LENGTH: 10
<212> TYPE: PRT
<213> ORGANISM: Artificial Sequence
```

```
<220> FEATURE:
<223> OTHER INFORMATION: Synthetic construct of novel peptide

<400> SEQUENCE: 41

Lys Tyr Arg Gln Arg Lys Lys Ser Lys Tyr
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 42

Lys Tyr Arg Gln Arg Lys Arg Ser Lys Tyr
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 43

Lys Tyr Arg Gln Arg Arg Lys Ser Lys Tyr
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 44

Lys Tyr Arg Gln Arg Arg Arg Ser Lys Tyr
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 45

Lys Tyr Arg Gln Lys Lys Lys Ser Lys Tyr
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 46

Lys Tyr Arg Gln Lys Arg Lys Ser Lys Tyr
1               5                   10

<210> SEQ ID NO 47
<211> LENGTH: 10
<212> TYPE: PRT
<213> ORGANISM: Artificial Sequence
<220> FEATURE:
```

```
<223> OTHER INFORMATION: Synthetic construct of novel peptide

<400> SEQUENCE: 47

Lys Tyr Arg Gln Lys Lys Arg Ser Lys Tyr
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 48

Lys Tyr Arg Gln Lys Arg Arg Ser Lys Tyr
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 49

Lys Tyr Arg Gln Arg Lys Lys Asn Tyr Lys
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 50

Lys Tyr Arg Gln Arg Lys Arg Asn Tyr Lys
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 51

Lys Tyr Arg Gln Arg Arg Lys Asn Tyr Lys
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 52

Lys Tyr Arg Gln Arg Arg Arg Asn Tyr Lys
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Synthetic construct of novel peptide
```

<400> SEQUENCE: 53

Lys Tyr Arg Gln Lys Lys Lys Asn Tyr Lys
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 54

Lys Tyr Arg Gln Lys Arg Lys Asn Tyr Lys
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 55

Lys Tyr Arg Gln Lys Lys Arg Asn Tyr Lys
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 56

Lys Tyr Arg Gln Lys Arg Arg Asn Tyr Lys
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 57

Lys Tyr Arg Gln Arg Lys Lys Ser Tyr Lys
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 58

Lys Tyr Arg Gln Arg Lys Arg Ser Tyr Lys
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Synthetic construct of novel peptide

```
<400> SEQUENCE: 59

Lys Tyr Arg Gln Arg Arg Lys Ser Tyr Lys
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 60

Lys Tyr Arg Gln Arg Arg Arg Ser Tyr Lys
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 61

Lys Tyr Arg Gln Lys Lys Lys Ser Tyr Lys
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 62

Lys Tyr Arg Gln Lys Arg Lys Ser Tyr Lys
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 63

Lys Tyr Arg Gln Lys Lys Arg Ser Tyr Lys
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 64

Lys Tyr Arg Gln Lys Arg Arg Ser Tyr Lys
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 65
```

Lys Tyr Lys Gln Arg Lys Lys Asn Lys Tyr
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 66

Lys Tyr Lys Gln Arg Lys Arg Asn Lys Tyr
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 67

Lys Tyr Lys Gln Arg Arg Lys Asn Lys Tyr
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 68

Lys Tyr Lys Gln Arg Arg Arg Asn Lys Tyr
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 69

Lys Tyr Lys Gln Lys Lys Lys Asn Lys Tyr
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 70

Lys Tyr Lys Gln Lys Arg Lys Asn Lys Tyr
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 71

Lys Tyr Lys Gln Lys Lys Arg Asn Lys Tyr
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 72

Lys Tyr Lys Gln Lys Arg Arg Asn Lys Tyr
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 73

Lys Tyr Lys Gln Arg Lys Lys Ser Lys Tyr
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 74

Lys Tyr Lys Gln Arg Lys Arg Ser Lys Tyr
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 75

Lys Tyr Lys Gln Arg Arg Lys Ser Lys Tyr
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 76

Lys Tyr Lys Gln Arg Arg Arg Ser Lys Tyr
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 77

Lys Tyr Lys Gln Lys Lys Lys Ser Lys Tyr

```
1               5                   10

<210> SEQ ID NO 78
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 78

Lys Tyr Lys Gln Lys Arg Lys Ser Lys Tyr
1               5                   10

<210> SEQ ID NO 79
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 79

Lys Tyr Lys Gln Lys Lys Arg Ser Lys Tyr
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 80

Lys Tyr Lys Gln Lys Arg Arg Ser Lys Tyr
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 81

Lys Tyr Lys Gln Arg Lys Lys Asn Tyr Lys
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 82

Lys Tyr Lys Gln Arg Lys Arg Asn Tyr Lys
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 83

Lys Tyr Lys Gln Arg Arg Lys Asn Tyr Lys
1               5                   10
```

<210> SEQ ID NO 84
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 84

Lys Tyr Lys Gln Arg Arg Arg Asn Tyr Lys
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 85

Lys Tyr Lys Gln Lys Lys Lys Asn Tyr Lys
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 86

Lys Tyr Lys Gln Lys Arg Lys Asn Tyr Lys
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 87

Lys Tyr Lys Gln Lys Lys Arg Asn Tyr Lys
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 88

Lys Tyr Lys Gln Lys Arg Arg Asn Tyr Lys
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 89

Lys Tyr Lys Gln Arg Lys Lys Ser Tyr Lys
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 90

Lys Tyr Lys Gln Arg Lys Arg Ser Tyr Lys
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 91

Lys Tyr Lys Gln Arg Arg Lys Ser Tyr Lys
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 92

Lys Tyr Lys Gln Arg Arg Arg Ser Tyr Lys
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 93

Lys Tyr Lys Gln Lys Lys Lys Ser Tyr Lys
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 94

Lys Tyr Lys Gln Lys Arg Lys Ser Tyr Lys
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 95

Lys Tyr Lys Gln Lys Lys Arg Ser Tyr Lys
1               5                   10

```
<210> SEQ ID NO 96
<211> LENGTH: 10
<212> TYPE: PRT
<213> ORGANISM: Artificial Sequence
<220> FEATURE:
<223> OTHER INFORMATION: Synthetic construct of novel peptide

<400> SEQUENCE: 96

Lys Tyr Lys Gln Lys Arg Arg Ser Tyr Lys
1               5                   10

<210> SEQ ID NO 97
<211> LENGTH: 20
<212> TYPE: DNA
<213> ORGANISM: Artificial Sequence
<220> FEATURE:
<223> OTHER INFORMATION: primer

<400> SEQUENCE: 97
ctgttgctag tggtgctgtt                                           20

<210> SEQ ID NO 98
<211> LENGTH: 23
<212> TYPE: DNA
<213> ORGANISM: Artificial Sequence
<220> FEATURE:
<223> OTHER INFORMATION: primer

<400> SEQUENCE: 98
cattctcctt gtgttccttt ggg                                       23

<210> SEQ ID NO 99
<211> LENGTH: 21
<212> TYPE: DNA
<213> ORGANISM: Artificial Sequence
<220> FEATURE:
<223> OTHER INFORMATION: primer

<400> SEQUENCE: 99
aggtcggtgt gaacggattt g                                         21

<210> SEQ ID NO 100
<211> LENGTH: 23
<212> TYPE: DNA
<213> ORGANISM: Artificial Sequence
<220> FEATURE:
<223> OTHER INFORMATION: primer

<400> SEQUENCE: 100
tgtagaccat gtagttgagg tca                                       23

<210> SEQ ID NO 101
<211> LENGTH: 23
<212> TYPE: DNA
<213> ORGANISM: Artificial Sequence
<220> FEATURE:
<223> OTHER INFORMATION: primer

<400> SEQUENCE: 101
cattctcctt gtgttccttt ggg                                       23

<210> SEQ ID NO 102
<211> LENGTH: 21
<212> TYPE: DNA
<213> ORGANISM: Artificial Sequence
<220> FEATURE:
<223> OTHER INFORMATION: primer
```

```
<400> SEQUENCE: 102
tgtggtcact atttgcctgt g                                       21

<210> SEQ ID NO 103
<211> LENGTH: 19
<212> TYPE: DNA
<213> ORGANISM: Artificial Sequence
<220> FEATURE:
<223> OTHER INFORMATION: primer

<400> SEQUENCE: 103
ccctgaagtc gaggagctg                                          19

<210> SEQ ID NO 104
<211> LENGTH: 19
<212> TYPE: DNA
<213> ORGANISM: Artificial Sequence
<220> FEATURE:
<223> OTHER INFORMATION: primer

<400> SEQUENCE: 104
ctgctgcacc tctaagcga                                          19
```